United States Patent [19]
Pelicic et al.

[11] Patent Number: 6,096,549
[45] Date of Patent: Aug. 1, 2000

[54] METHOD OF SELECTION OF ALLELIC EXCHANGE MUTANTS

[75] Inventors: Vladimir Pelicic; Jean-Marc Reyrat; Brigitte Gicquel, all of Paris; Christophe Guilhot, Issy les Moulineaux; Mary Jackson, Paris, all of France

[73] Assignee: Institut Pasteur, Paris, France

[21] Appl. No.: 08/872,917

[22] Filed: Jun. 11, 1997

Related U.S. Application Data

[63] Continuation-in-part of application No. 08/661,658, Jun. 11, 1996, Pat. No. 5,843,664.

[51] Int. Cl.⁷ .............................. C12N 1/21; C12N 15/00
[52] U.S. Cl. .................... 435/473; 435/252.3; 435/253.1
[58] Field of Search .................................. 435/4, 6, 172.1, 435/172.3, 252.1, 252.3, 253.1, 320.1, 473

[56] References Cited

U.S. PATENT DOCUMENTS 5,807,723  9/1998  Aldovini et al. ........................ 435/477

FOREIGN PATENT DOCUMENTS

WO 92/01796  2/1992  WIPO .
WO 92/22326  12/1992  WIPO .

OTHER PUBLICATIONS

Quandt, J. et al., "Versatile Suicide Vectors Which Allow Direct Selection for Gene Replacement in Gram–Negative Bacteria," *Gene*, pp. 15–21 (1993).

Stibitz, S., "Use of Conditionally Counterselectable Suicide Vectors for Allelic Exchange," *Meth. Enzymol*, vol. 235, pp. 458–465 (1994).

Kalpana, G.V. et al., "Insertional Mutagenesis and Illegitimate Recombination in Mycobacteria," *Proc. Nat'l. Acad. Sci. USA*, vol. 88, pp. 5433–5437 (Jun. 1991).

Cirillo, Jeffrey D. et al., "A Novel Transposon Trap for Mycobacteria: Isolation and Charaterization of IS1096," *J. Bacteriol.*, vol. 173, No. 24, pp. 7772–7780 (Dec. 1991).

McAdam, R. et al., "In Vivo Growth Characteristics of Leucine and Methionine Auxotrophic Mutants of Mycobacterium bovis BCG Generated By Transposon Mutagenesis," *Infection and Immunity*, vol. 63, No. 3, pp. 1004–1012 (Mar. 1995).

Pelicic, V. et al., "Expression of the Bacillus Subtilis sacB Gene Confers Sucrose Sensitivity On Mycobacteria," *J. Bacteriol.*, vol. 178, No. 4, pp. 1197–1199 (Feb. 1996).

Sander, P. et al., "rpsL: A Dominant Selectable Marker for Gene Replacement In Mycobacteria," *Mol. Microbiol.*, vol. 16, No. 5, pp. 991–1000 (1995).

Reyrat, J.M. et al., "The Urease Locus of Mycobacterium Tuberculosis and Its Utilization for the Demonstration of Allelic Exchange in Mycobacterium Bovis Bacillus Calmette–Guerin," *Proc. Nat'l. Acad. Sci. USA*, vol. 92, pp. 8768–8772 (Sep. 1995).

Norman, E. et al., "Gene Replacement by Homologous Recombination In Mycobacterium Bovis BCG," *Mol. Microbiol.*, vol. 16, No. 4, pp. 755–760 (1995).

Marklund, B.I. et al., "Gene Replacement Through Homologous Recombination In Mycobacterium Intracellular," *J. Bacteriol.*, vol. 177, No. 21, pp. 6100–6105 (Nov. 1995).

Husson, R. et al., "Gene Replacement and Expression of Foreign DNA in Mycobacteria," *J. Bacteriol.*, vol. 172, No. 2, pp. 519–524 (Feb. 1990).

Balasubramanian, V. et al., "Allelic Exchange in Mycobacterium Tuberculosis With Long Linear Recombination Substrates," *J. Bacteriol.*, vol. 178, No. 1, pp. 273–279 (Jan. 1996).

Aldovini, A. et al., "The uraA Locus and Homologous Recombination In Mycobacterium Bovis BCG," *J. Bacteriol.*, vol. 175, No. 22, pp. 7282–7289 (Nov. 1993).

Guilhot et al. (1994) Efficient transposition in mycobcteria: construction of Mycobacterium smegmatis insertional mutant libraries. J. Bacteriol. 176:535–539, Jan. 1994.

*Primary Examiner*—Robert A. Schwartzman
*Attorney, Agent, or Firm*—Finnegan, Henderson, Farabow, Gattett & Dunner, L.L.P.

[57] ABSTRACT

A process for replacing a nucleotide sequence in the genome of a mycobacterium strain comprises the steps of:

a) providing a vector containing SacB gene coding for levane saccharase enzyme and a nucleotide sequence of interest;

b) transfecting the mycobacterium strain with the vector;

c) selecting clones of the resulting transfected mycobacteria for replacement of the nucleotide sequence of interest by propagating the transfected clones in a culture medium supplemented with sucrose; and d) isolating the recombinant strain.

The process is useful for positive selection of allelic exchange mutants, such as in *Mycobacterium tuberculosis* complex.

12 Claims, 15 Drawing Sheets

SEQ ID NO 3
IRLEFT
GGCTCTTCGCAGTTGAGGGTGTAGAG.....CTCTACACCGTCAAGTGGAAGAGCC

IS 1096::KM
β →
← α

SEQ ID NO 4
IRRIGHT

SEQ ID NO 5  MYC1  CCATTAC
SEQ ID NO 6  MYC2  AAAAAAC
SEQ ID NO 7  MYC3  TGATTAC
SEQ ID NO 8  MYC4  CATTAGC
SEQ ID NO 9  MYC5  GAATTAGC
SEQ ID NO 10 MYC6  GTCAAACG
SEQ ID NO 11 MYC7  CCATTAGG

DR

CCATTAC
AAAAAAC
CGATTAC
CATTAGC
GAATTAGC
GTCAAACC
CCATTAGG

DR

TB (7 PB)      BCG (8 PB)

FIG. 15

METHOD OF SELECTION OF ALLELIC EXCHANGE MUTANTS

This application is a continuation-in-part of application Ser. No. 08/661,658 filed Jun. 11, 1996 U.S. Pat. No. 5,843,664.

BACKGROUND OF THE INVENTION

Recently developed techniques for introducing and expressing genes in mycobacteria have opened the way for molecular genetic manipulation as a means to obtain further understanding of these species (Jacobs et al., 1991). Usually, virulence factors are genetically characterized following Koch's molecular postulates (Falkow, 1988): (i) cloning of the gene of interest; (ii) effects on the virulence of specific inactivation of the gene; and (iii) restoration of the pathogenicity by complementing with the wild-type allele. However, the genetic analysis of mycobacteria has been hampered by a lack of efficient tools for generating defined mutants by homologous recombination (Jacobs, 1992).

The 'reverse genetics' approach to understanding gene function is to specifically disrupt the gene of interest by exploiting the homologous recombination properties of the cell to replace the functional allele with an inactivated copy (Ruvkun and Ausubel, 1981). Usually, the gene is inactivated by the insertion of an antibiotic-resistance marker, such that the recombination event is easily detected on a selective medium. It was demonstrated that this methodology is applicable to *Mycobacterium smegmatis* using the pyrF gene (Husson et al., 1990). However, performing allelic exchange has been relatively cumbersome due to the rarity of double-cross-over events, requiring an extensive screening to isolate a gene-exchange mutant. This method has proven particularly inefficient in slow-growing mycobacteria where homologous recombination is less frequent than illegitimate recombination, i.e., recombination at a site other than the selected gene by an unknown mechanism. Several workers have been unable to detect any gene replacement (Aldovini et al., 1993; Kalpana et al., 1991). However, several recent studies have succeeded in identifying allelic exchange, albeit at low frequency, in slow-growing mycobacteria (Marklund et al., 1995; Norman et al., 1995; Reyrat et al., 1995; Balasubramanian et al., 1996). Clearly, allelic exchange would greatly benefit from a system allowing positive selection of mutants resulting from gene replacement.

High levels of illegitimate recombination and low frequency of recombination have also been described in gene-replacement experiments in eukaryotic cells and some bacteria (Cai and Wolk, 1990; Desomer et al., 1991). These problems can be overcome by employing a double-selection strategy (Stibitz, 1994). The vector used for mutagenesis should bear an antibiotic marker for the primary selection of transformants, and a second marker with a conditionally dominant lethal effect to counter-select clones which have lost the vector DNA, eliminating the need for extensive screening. No counter-selectable marker was available for mycobacteria until recently, when the rpsL gene was shown to exhibit a dominant lethal effect in *M. smegmatis*. It was used to demonstrate that double selection is possible in this bacterium (Sander et al., 1995).

There has existed a need to design a general method for gene exchange mutagenesis, which would overcome the problems arising from high levels of illegitimate recombination and low frequency of homologous recombination. A possible strategy, based on the use of much longer stretches of linear homologous DNA (20 kb or more) was recently proposed (Balasubramanian et al., 1996). In this way, it was shown that the frequency of homologous recombination for the M. tuberculosis leuD gene could be increased. The proportion of allelic exchange mutants rose from an undetectable level to approximately 6% of the transformants (Balasubramanian et al., 1996). However, a possible limitation to this methodology is the fact that manipulation of cosmids is relatively difficult due to their extensive length.

SUMMARY OF THE INVENTION

The present invention overcomes the difficulties described in the prior art by employing a conditionally dominant lethal marker in a double-selection strategy as described by Stibitz (1994). This marker, present on a suicide delivery vector, is inserted into the chromosome of the clones resulting from single homologous recombination or illegitimate recombination events, leading to their death on selective medium. The resulting effect is an increase of the proportion of allelic exchange mutants, making the screening of transformants easier. Recently, one counter-selectable marker has been described in *M. smegmatis* and used to demonstrate that positive selection of allelic exchange mutants is possible in this bacterium: the rpsL gene conferring a dominant phenotype of sensitivity to streptomycin (Sander et al., 1995).

This invention provides, for the first time, a second counter-selective marker: the *Baillus subtilis* SacB gene, conferring sensitivity to sucrose (also described in Pelicic et al., *Mol. Microbiol.* 1996). SacB is a particularly powerful tool because it can be used for the positive selection of mutants in either single-step or two-step selection strategies. In a single-step protocol, a suicide vector is electroporated into *M. smegmatis* and the allelic exchange mutants are directly selected on sucrose. In a two-step selection, a single recombination transformant is first selected and propagated in liquid broth to allow a second crossing-over to occur. Then by plating on sucrose, the mutants that have lost the SacB gene during the second crossing-over can be positively selected. Prior to the present invention, it was not apparent that this latter possibility should be of particular interest in slow-growing mycobacteria. Indeed, a one-step selection would be unadapted for numerous genes where double recombinants are undetectable in a classical experiment (Jackson pers. comm.; Ruvkin and Ausubel, 1981).

Even if SacB was shown to confer sucrose sensitivity on slow-growing mycobacteria (Pelicic et al., *J. Bacteriol.* 1996), the demonstration of its use as a marker for positive selection of allelic exchange mutants had not been done prior to this invention. Thus, for the first time, a two-step selection protocol was explored in slow-growing mycobacteria with the ureC gene as a model.

Accordingly, this invention provides a process for replacing a nucleotide sequence in the genome of a mycobacterium strain. The process comprises providing a vector containing a SacB gene coding for levane saccharase enzyme and a nucleotide sequence of interest. The mycobacterium strain is transfected with the vector by, for example, electroporation or conjugation. Clones of the resulting transfected mycobacteria are selected for replacement of the nucleotide sequence of interest by propagating the transfected clones in a culture medium supplemented with sucrose. The recombinant strain can be isolated, if desired. Typical mycobacterium strains suitable in the processes of this invention include *M. tuberculosis, M. smegmatis, M. bovis, M.bovis-BCG, M. africanum, M. microti, M. avium,*

*M. gordonae*, and *M. leprae*. In a preferred embodiment of this invention, the mycobacterium is a slow growing mycobacterium.

In a prefered embodiment of this invention, the vector employed in the process contains a marker gene, and the selection step is preceded by a first selection step of the clones by propagating the clones in a culture medium supplemented with a selection molecule. For example, the marker gene can be a gene coding for resistance to an antibiotic, such as gentamycin or kanamycin.

In another embodiment of this invention, the vector employed in the process contains a replication origin, which is functional in, e.g., *E.coli*.

The nucleotide sequence of interest can be an endogenous gene of the mycobacteria to be transfected. The nucleotide sequence can be modified by addition, substitution, or deletion of at least one nucleotide. The terms "substitution" and "deletion" refer to single base pair changes. Preferably, the modified nucleotide sequence does not contain more than 3% substitutions or deletions within its total length. An "addition" may refer to the whole sequence of a gene that can be inserted into the middle of the nucleotide sequence contained in the vector (where the nucleotide sequence represents the counterpart of the sequence to be replaced in the genome of the mycobacterium). For example, the addition may be the insertion of an antibiotic resistance gene or a gene encoding an exogenous antigen or immunogen.

Alternatively, the nucleotide sequence of interest can be exogenous with respect to the mycobacteria to be transfected. An exogenous nucleotide sequence according to the present invention is a nucleotide sequence that is not naturally present in the mycobacteria to be recombined or which is present in said mycobacteria at another location than the location at which it will be inserted by the allelic exchange method of the invention. Such an exogenous sequence comprises the exogenous nucleotide sequence of interest, which is bordered at its 5' and 3' ends by at least a homologous nucleotide sequence of 1 kb in length, said homologous nucleotide sequence being the counterpart in the plasmid of the mycobacterial genomic sequence in order to allow the allelic exchange event to take place.

In another embodiment of the invention, the nucleotide sequence to be replaced can be a plasmid or a chromosomal nucleotide sequence.

In still another embodiment, the nucleotide sequence of interest can be a hybrid molecule coding for a fusion polypeptide. This invention also provides a process of the type described, wherein the fusion polypeptide contains an antigenic determinant heterologous with respect to the mycobacterium strain to be transfected, the antigenic determinant being much more recognized by the sera of patients than the initial endogenous antigenic determinant.

Suitable antigenic determinants that may be used in the processes of this invention include, but are not limited to:

1) the 6 kD early secretory antigenic target (ESAT-6) described by Sorensen et al., (1995) (for example, the ESAT-6 may be inserted in *M. bovis* BCG strain as a fusion sequence with a known non-essential nucleotide sequence of *M. bovis* BCG, and thus provide an improvement to the conventionally used BCG strains because the recombinant strains will be able to express immunogenic determinants that are specific to *M. tuberculosis*. These recombinant strains may then provide an improved means to make efficient vaccine preparations);
2) the 45/47 kD immunogenic protein from *M. tuberculosis*, described in International patent application PCT/FR96/0166;
3) the surface antigen from the hepatitis B virus (HBsAg) described in French patent application No. FR 7921811; and
4) nucleotide sequences coding for all or part of HIV glycoproteins, e.g., the genome sequences from HIV-1 disclosed in patent applications GB 8324800, EP 84401834 or EP 85905513; or the genome sequences for HIV-2 described in patent application EP 87400151.

This invention also provides recombinant mycobacterium strains. The strains can have a modified nucleotide sequence in their genomes, differ from wild-type sequences of said mycobacterium, and the recombinant mycobacterium strains may or may not contain sequences from an insertion vector.

This invention further provides recombinant vectors, which are particularly suitable for use in the invention.

In addition, this invention provides a method of selecting mycobacteria sensitive to sucrose. The method comprises cultivating mycobacteria in a culture medium supplemented with sucrose; cultivating in parallel the same mycobacteria in a culture medium without sucrose; and selecting clones sensitive to sucrose having a genome that contains SacB gene.

Finally, this invention provides method to evaluate the virulence mechanisms of *Mycobacterium tuberculosis*. It is well known that an understanding of bacterial virulence mechanisms is highly dependent on the design of efficient mutagenesis systems. Such efficient mutagenesis systems have not previously been available for *Mycobacterium tuberculosis*. Thus, this invention provides for the first time, a system enabling the positive selection of Mycobacterium insertional mutants having lost the delivery vector. This methodology allows the construction of *M. tuberculosis* transposon mutants libraries containing greater than 10% mutants, far exceeding the number theoretically required to obtain at least one insertion in every non-essential gene.

Transposon mutagenesis of mycobacteria using the methods and products according to the present ivention are also useful in the design of random recombinant auxotrophic mycobacteria. Auxotrophs are useful as new vaccine candidates where, for example, the mutants affected in virulence genes are selected as clones that are unable to survive for a long period of time in macrophages. These mycobacterial mutants are also useful to provide additional information concerning residual virulence and protective effect. This valuable tool will allow, for the first time, construction of new vaccines against tuberculosis.

A preferred vector for use in the design of a transposon mutants library is a vector carrying:

a) an insertion sequence containing a selection marker gene such as, the insertion sequence IS1906 interrupted by a kanamycin resistance gene (IS1096:Km);
b) a conditionally functional origin of replication, such as a conditional thermosensitive origin of replication; and
c) the SacB gene.

BRIEF DESCRIPTION OF THE DRAWINGS

This invention will be more fully understood with reference to the drawings in which:

FIG. 1 is a Southern-blot analysis of representative clones resulting from homologous recombination obtained either by a one-step selection or by a two-step selection on sucrose. Two $Ura^+$ and two $Ura^-$ clones are presented. WT indicates *M. smegmatis* wild-type DNA. Genomic DNA was digested with SphI and hybridized with a 2.5 kbp SphI fragment carrying the pyrF gene.

FIG. 2 shows a general strategy for generating unmarked mutations in mycobacteria using a two-step selection methodology. The first selection is performed on plates with gentamicin (LUG). The second selection step is performed on LUS to select positively for the clones that have lost the SacB gene; pyrF* and SacB* indicate mutant alleles of those genes.

FIG. 3 is a Southern-blot analysis of various clones resulting from the integration of pPR34 during a two-step selection strategy as described in FIG. 2. Genomic DNA was digested with SphI and hybridized with the pyrF probe.

FIG. 4 is a Southern-blot analysis of representative clones, 5 Ure$^-$ and 6 Ure$^+$, obtained after the selection on 2% sucrose (SECOND STEP). Two controls have been included, BCG is for *M. bovis* BCG wild-type DNA and BCG::pPR24 is a single recombinant. Genomic DNA was digested with PstI and hybridized with the pPR24 vector as a probe.

FIG. 5 shows a general strategy for allelic exchange mutagenesis using a two-step selection on 2% sucrose. In the first step, a single recombinant is selected on kanamycin or gentamycin. In the second step, clones that have lost the SacB gene are positively selected on 2% sucrose. SacB* indicate a mutant allele of the SacB gene. Abbreviations: ureA, ureB, and ureC are the three subunits of the mycobacterial urease (Reyrat et al., 1995); Km, Tn903 gene encoding kanamycin resistance; Gm, aacCI gene encoding gentamicin resistance; ori, *E. coli* origin of replication.

FIG. 6 is a map describing plasmid pPR26 (C.N.C.M. No. I-1729).

FIG. 7 is a map describing plasmid pPR34 (C.N.C.M. No. I-1731).

FIG. 8 is a map describing plasmid pPV23(1) (C.N.C.M. No. I-1726).

FIG. 9 is a map describing plasmid pPR27 (C.N.C.M. No. I-1730).

FIG. 10 is a map describing plasmid pPR25 (C.N.C.M. No. I-1728).

FIG. 11 is a map describing plasmid pPR24 (C.N.C.M. No. I-1727).

FIG. 12 is a map describing plasmid pPR2 (C.N.C.M. No. I-1725).

FIG. 13 describes the design of new vectors for positive selection of rare genetic events (pPR27 is shown as an example). Only single restriction sites, which can be used for the subsequent cloning of a transposon or a mutant allele, are shown.

FIG. 14 is a Southern-blot analysis of representative *M. tuberculosis*::Tn5368 clones and expected schematic hybridization patterns for a transposition mutant. Five mutants were picked at random (clones 1 to 5). *M. tuberculosis* 103 DNA (WT) was included as a control and as expected showed no hybridization signal. Genomic DNA was digested with BamHI or XhoI and probed for hybridization with the pPR32 vector. Molecular weights are indicated in kb.

FIG. 15 depicts sequences of cloned insertion sites for several *M. tuberculosis* and *M. bovis* BCG transposition mutants. Approximately 500 bp of DNA flanking the transposon were sequenced using IS1096 outward primers α and β, but only direct repeats (DR) are shown. Imperfectly repeated nucleotides are underlined.

DESCRIPTION OF PREFERRED EMBODIMENTS

Figure 1:
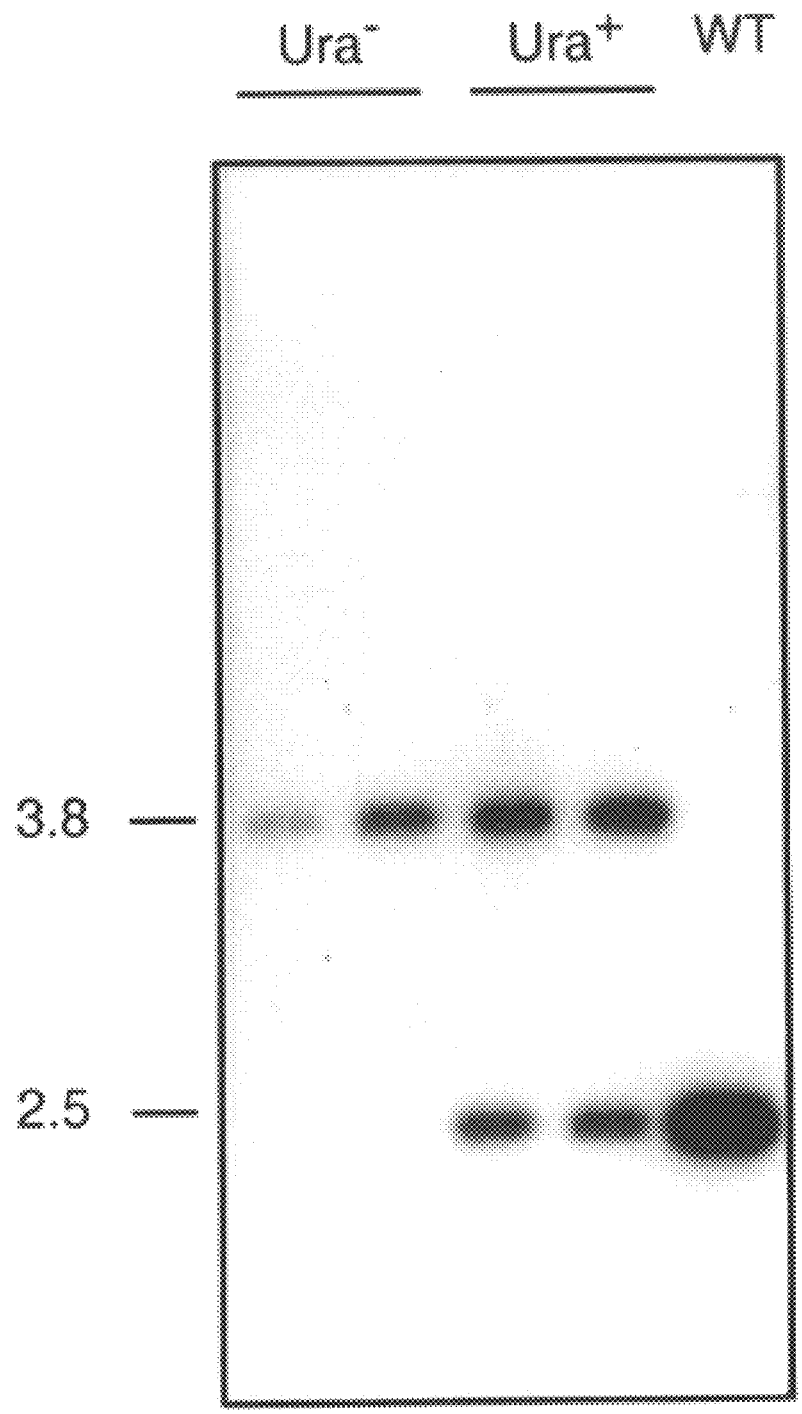

It has been demonstrated that the Bacillus subtilis SacB gene, encoding the secreted enzyme levansucrase (sucrose: 2,6-β-D-fructan 6-β-*D-fructosyltransferase;* EC 2.4.1.10), confers sucrose sensitivity to mycobacteria on 10% sucrose (Pelicic et al., *J. Bacteriol.* 1996). The efficiency of selection, $5 \times 10^{-4}$ for *M. smegmatis* and $10^{-6}$ for *Mycobacterium bovis* BCG, is comparable to that for other bacteria where SacB has been used for positive selection of allelic exchange (Cai and Wolk, 1990; Cianciotto et al., 1988; Kaniga et al., 1991; Kamoun et al., 1992; Schafer et al., 1994; Schweizer, 1992). The possibility of using SacB as a positive-selection system for gene-replacement events in mycobacteria was tested. The pyrF gene of *M. smegmatis* was chosen as a model because it has previously been used in homologous recombination experiments in this species. pyrF mutants are uracil auxotrophs and can thus be easily screened. It was found that pyrF mutants resulting from allelic-exchange events were readily identified by either a one-step or a two-step selection on sucrose. Using a two-step selection, uracil auxotrophic mutants were isolated with an unmarked, defined mutation in the pyrF gene. These results illustrate how SacB can be used to facilitate experiments involving allelic-exchange events in mycobacteria.

One-step Selection of PyrF Allelic Exchange pJQ200 is a cloning vector carrying a gentamycin-resistance gene active mycobacteria, and the SacB gene of *B. subtilis* (Quandt and Hynes, 1993). The pyrF gene disrupted by the aph cassette, conferring resistance to kanamycin, (pyrF::Km), was obtained from pY6002 (Husson et al., 1990) and inserted in pJQ200 to give pPR26. pPR26 was used to transform *M. smegmatis* by electroporation. The transformants resulting from homologous integration were selected on Luria-Bertani (L) medium supplemented with uracil (LU), and contained either (i) kanamycin (LUK) as a classical test for the frequency of recombination or (ii) kanamycin and sucrose (LUKS) to assess the possibility of sucrose selection. The electroporation of 1 μg of vector resulted in approx. 100 transformants on LUK and only approx. 5 on LUKS plates, a 20-fold decrease. In the same conditions, pY6002, which lacks the SacB gene, gave the same number of colonies on LUK and LUKS plates (data not shown). Thus SacB, present on pPR26, is responsible for the death of the majority of the transformants when selection is performed on sucrose.

The phenotypes of the transformants were characterized by replica plating on different selective media. Most of the clones (95%) selected on LUK plates were kanamycin resistant (Km$^R$), gentamicin resistant (Gm$^R$), sucrose sensitive (Suc$^S$), uracil positive (Ura$^-$) and resulted from single recombination events in the pyrF gene (Table 1).

Table 1. Effects of the presence of sucrose on the proportion of pyrF allelic-exchange mutants recovered from a one-step selection after transformation with pPR26.

TABLE 1

Effects of the presence of sucrose on the proportion of pyrF allelic-exchange mutants recovered from a one-step selection after transformation with pPR26.

| | Percent of total clones (%)[a] | |
|---|---|---|
| Growth medium | Ura$^-$, Km$^R$, Gm$^S$ (allelic exchange) | Ura$^-$, Km$^R$, Gm$^R$ (simple recombination) |
| LUK | 5 | 95 |
| LUKS | 100 | 0 |

[a]Mean value of two independent experiments.

Genomic DNA from these transformants was analyzed by Southern blotting with a pyrF probe. These clones contained a complete copy of pPR26 inserted into the pyrF gene, thus possessing both an intact (2.5 kbp) and an inactivated copy of pyrF (3.8 kbp) (FIG. 1). The remaining clones 5% were true uracil auxotrophs, with the phenotype $Km^R$, $Gm^S$, $Suc^R$, $Ura^-$. The endogenous allele of the pyrF gene, corresponding to a SphI fragment of 2.5 kbp on a Southern blot, had been replaced by the inactivated copy corresponding to a fragment of 3.8 kbp (FIG. 1). The increase of 1.3 kbp corresponds to the size of the kanamycin-resistance gene which was used to inactivate pyrF. Moreover, no hybridization signal was detected in the auxotrophs when the vector pJQ200 was used as a probe (data not shown), indicating that the vector sequence had been lost.

All the transformants (100%) selected on the LUKS plates exhibited the $km^R$, $Gm^S$, $Suc^R$, $Ura^{31}$ phenotype and were uracil auxotrophs generated by allelic exchange at the pyrF gene (Table 1). This was confirmed by Southern-blot analysis, which gave hybridization patterns indistinguishable from those observed for the auxotrophs obtained on LUK plates. See (FIG. 1). One-step selection on sucrose was 100 efficient, because all of the clones corresponding to single recombination events (incorporation of the entire vector bearing the SacB gene) were eliminated. Thus, when a suicide vector bearing the SacB gene is used for the homologous recombination experiments, mutants resulting from an allelic exchange can be directly selected by plating on sucrose.

Two-step Selection Method

The possibility of selecting allelic-exchange events in two steps was next investigated. This procedure might be useful if the frequency of gene exchange for a gene of interest is too low to recover mutants in one step. For the first step, an individual clone was chosen at random from those obtained on a LUK plate in the previous experiment. It was verified that this clone corresponded to a single recombination event in the pyrF gene by phenotypic ($km^R$, $Gm^R$, $Suc^S$, $Ura^{30}$) and Southern-blot analysis. The clone was propagated overnight in 7H9 medium (Difco) supplemented with uracil (without antibiotic selection) to allow a deletion-recombination event to occur at the pyrF locus. Any such event could either eliminate the wild-type or the interrupted allele of the pyrF gene. The culture was spread on LUKS plates (step 2) to select cells which had lost the SacB gene. Several thousands of colonies were obtained and approx. 200 clones were analyzed. Two-thirds were uracil auxotrophs as verified by phenotypic analysis (Table 2) and Southern hybridization (FIG. 1). The remaining colonies (⅓), although $Suc^R$, were not uracil auxotrophs ($km^R$, $Gm^R$, $Suc^R$, $Ura^{30}$) and presumably corresponded to clones with a mutation in the SacB gene.

TABLE 2

Effects of the presence of sucrose on the proportion of pyrF allelic-exchange mutants recovered from a two-step selection.

| | | Percent of total clones (%)[b] | | |
|---|---|---|---|---|
| Transforming DNA | Growth medium | $Ura^-$, $Gm^S$ $Suc^R$ (allelic exchange) | $Ura^+$, $Gm^R$ $Suc^R$ (SacB mutants) | $Ura^+$ (revertants) |
| pPR28 | LUKS | 66 | 34 | ND |
| pPR26 | LUS | 35 | 7 | 58 |
| pPR34 | LUS | 27 | 4 | 69 |

[a]Medium used in the second step of selection.
[b]At least 192 clones were analyzed in each experiment.
[ND]Not detectable Genomic DNA was probed with pJQ200 by Southern blotting: this showed that the SacB mutations were either point mutations (no change of vector size) or 2 kbp insertions possibly resulting from the insertion of a transposable element (data not shown). It is possible that the trapped sequence corresponds to IS1096, which was discovered in M. smegmatis using a similar methodology with β-galactosidase as a reporter gene (Cirillo et al., 1991). This suggests that SacB can be used as a transposon trap in M. smegmatis, as it has been used in Escherichia coli (Gay et al., 1985).

The experiment was repeated, but with the second selection step on sucrose plates without kanamycin (LUS). Three times more colonies were obtained at the same dilution than by selection on LUKS plates. Thus, the majority of the clones on LUS plates were expected to be sensitive to kanamycin and to have resulted from loss of the interrupted allele of pyrF (pyrF::Km), and thus the Km cassette. This was verified by phenotypic ($Km^S$, $Gm^S$, $Suc^R$, $Ura^{30}$) (Table 2) and Southern-blot analysis (FIG. 1). A small proportion of the clones (7%) resulted from mutations in the SacB gene. But a significant proportion of the clones obtained were uracil auxotrophs (1 in 3), and corresponded to allelic-exchange mutants. Therefore, positive selection of allelic-exchange events is possible on sucrose using a two-step methodology, even when no antibiotic selection was applied during the second step of selection.

Generation of Unmarked Mutants

Figure 2:
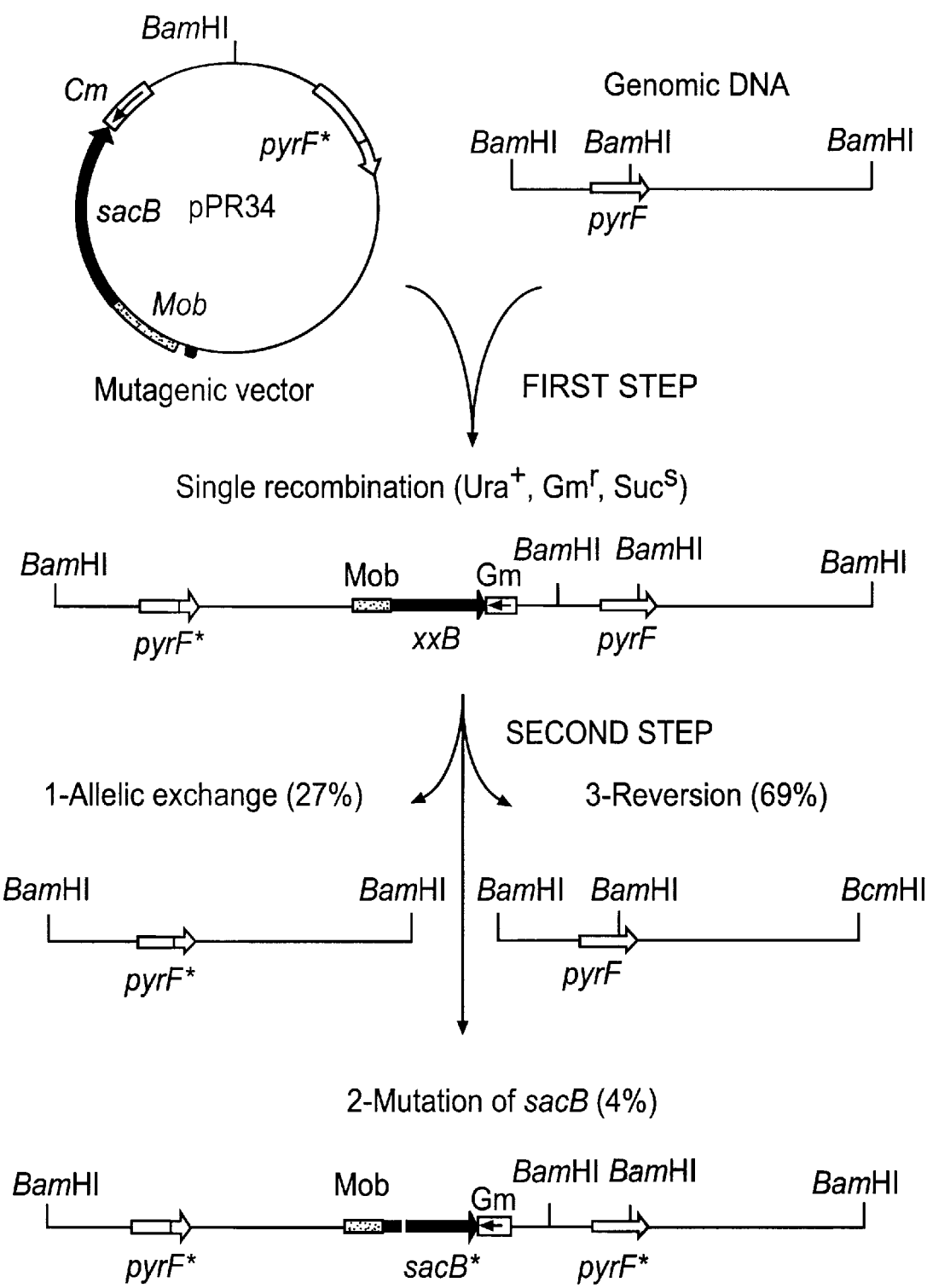

The feasibility of a two-step selection, in the absence of antibiotic selection during the second step, suggested that it might be possible to generate unmarked mutants as described for other bacteria (Donnenberg et al., 1991; Ried and Colimer, 1987; Schafer et al., 1994; Soupene et al., 1995). The aph gene was excised with BamHI from the mutated allele pyrF::Km (Husson et al., 1990) and a frameshift mutation was generated by blunting the ends with T4 DNA polymerase and religating. This unmarked mutated copy of the pyrF gene (pyrF) was inserted into pJQ200 to generate pPR34 (FIG. 2).

pPR34 was used to transform M. smegmatis by electroporation, and clones resulting from a single homologous recombination event were selected on LU supplemented with gentamicin (LUG): the PJQ200 vector carries the sacCl gene conferring gentamicin resistance (Quandt and Hynes, 1993). The phenotype and Southern-blot analyses confirmed that the selected clones resulted from a single cross-over in the pyrF gene (data not shown). As described above, the second step of selection was performed on LUS medium. The clones were replica plated onto M63 minimal medium. Approximately ⅓ of the clones were unable to grow on minimal medium and were thus uracil auxotrophs (Table 2). This is consistent with the results of the previous experiment with pPR26, with no selective pressure for the antibiotic resistance during the second step (Table 2).

Figure 3:
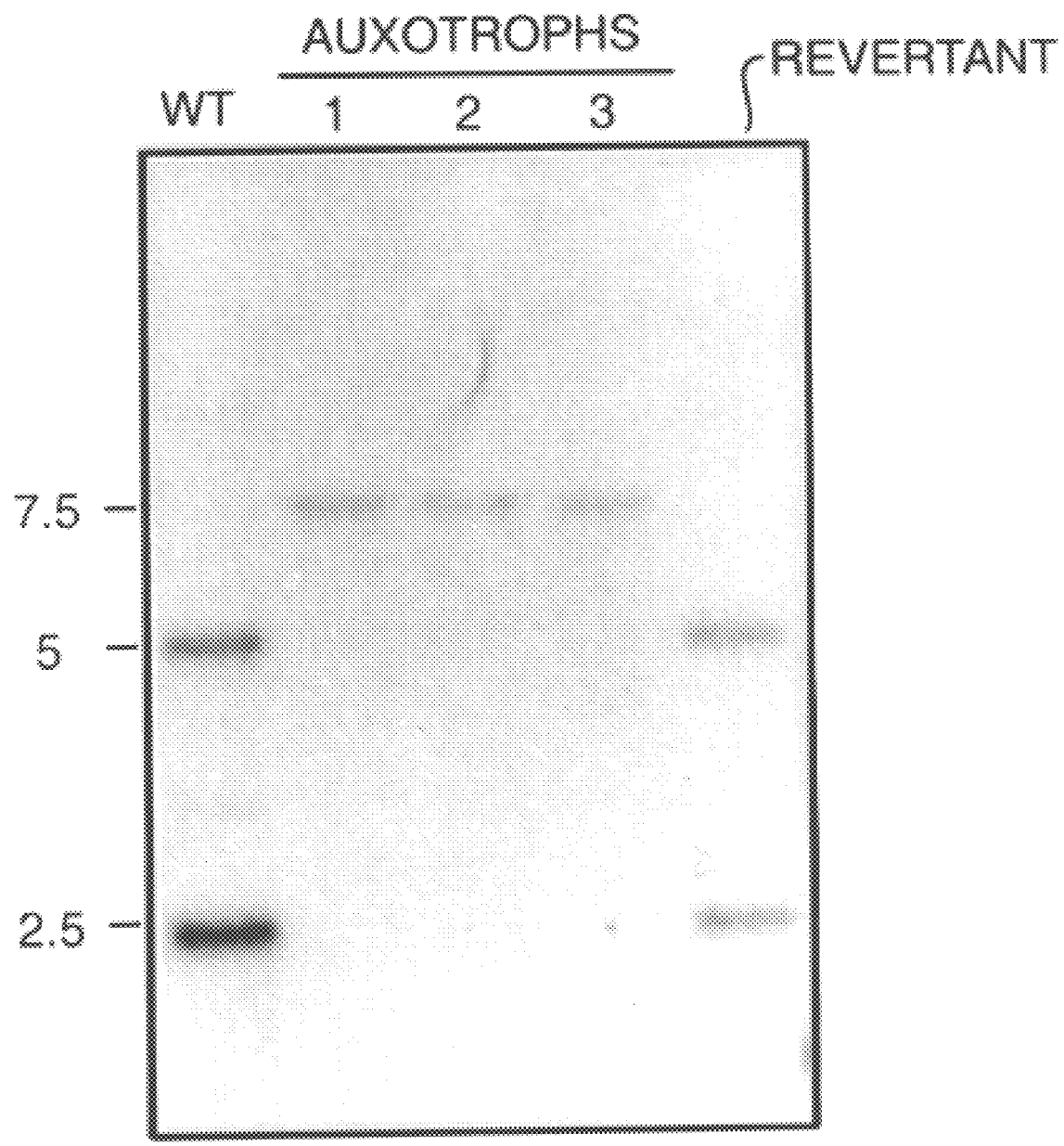

As the frameshift mutation introduced into the pyrF gene destroyed a BamHI site, allelic-exchange mutants identified by their auxotrophic phenotype should have a different hybridization pattern in a Southern-blot analysis with BamHI-cut DNA. Several $Ura^{30}$ revertants and $Ura^{31}$ mutants were analyzed by Southern blotting. As expected, the revertant clones presented two fragments of 2.5 kbp and 5 kbp hybridizing to the pyrF probe. The unmarked auxotrophic mutants gave a single hybridizing BamHI fragment of 7.5 kbp, confirming the loss of the central BamHI site (FIG. 3). Thus, a two-step selection with sucrose selection in the second step enabled us to isolate unmarked mutants carrying a known, specific lesion in the pyrF gene.

In summary, a double-selection strategy was recently adapted to M. smegmatis using the rpsL gene as a counterselectable marker (Sander et al., 1995). However, its applicability to slow-growing mycobacteria has not been described. rspL is a dominant marker conferring susceptibility to streptomycin to a streptomycin-resistant strain which carries a mutation in the endogenous rpsL allele. When used as a counter-selectable marker, rpsL leads to allelic-exchange mutants resistant to streptomycin, an antibiotic, which is still a common component of several combined antituberculosis chemotherapeutic regimens (WHO, 1991).

SacB presents several interesting characteristics making it a useful counter-selectable marker for the positive selection of gene-exchange events in mycobacteria. First, SacB does not require an antibiotic-resistant strain to induce lethality. Second, SacB can be used in two-step selection strategies. This approach will prove useful in cases where the frequency of allelic exchange for the gene of interest is too low for one-step selection. Third, the efficiency of selection on sucrose in a two-step strategy is sufficiently high to detect rare deletions that give rise to unmarked defined mutants. Although antibiotic markers are useful for genetic studies, an unmarked mutant is necessary when generating strains for use as new vaccines. Moreover, in the construction of strains with multiple mutations there is no need for a corresponding number of antibiotic-resistance markers.

The expression of SacB, the *Baillus subtilis* gene encoding levansucrase, is lethal to mycobacteria in the presence of 10% sucrose. The use of SacB as a marker for positive selection of gene-replacement events into Mycobacterium smegmatis is herein described. A sucrose counter-selectable suicide plasmid was used to deliver an inactivated copy of the pyrF gene (pyrF::Km) into the *M. smegmatis* genome. Only uracil auxotroph clones, resulting from replacement of the endogenous pyrF allele, survived in a one-step selection on plates containing kanamycin and 10% sucrose. This demonstrated that selection on sucrose against the maintenance of the vector bearing the SacB gene is 100% efficient, enabling the positive selection of allelic-exchange mutants. Two-step selection is also feasible; it was used to construct unmarked pyrF mutants in which the gene was inactivated by a frameshift mutation. This method of generating unmarked, directed mutations is rapid and simple, making it a powerful tool for the genetic characterization of mycobacteria.

Transposon Mutagenesis

Transposon mutagenesis, which has often been used for the identification of bacterial virulence factors, is one of the most powerful methods of mutagenesis. It involves the use of a mobile element to disrupt genes randomly in the chromosome upon transposition. Using a conventional strategy, i.e., delivering the transposon on a vector unable to replicate in mycobacteria, transposition has been demonstrated in *M. bovis* BCG, a member of the *M. tuberculosis* complex, for several mycobacterial transposons, including IS1096 described by McAdam et al., 1995 and IS6120 and IS6100 derivatives (unpublished data). Because electroporation efficiencies and transposition frequencies are very low, no more than 100 mutants per experiment have been obtained (McAdam et al., 1995). However, as *M. tuberculosis* contains an estimated 3,000 genes, approximately 10,000 mutants would be required to obtain a mutation in each of them. Suicide delivery vectors are thus not suitable for the construction of representative libraries of mutants. Another method for creating mutants is allelic exchange mutagenesis. Recently, low-frequency allelic exchange was demonstrated in bacteria of the *M. tuberculosis* complex, again using a suicide delivery vector (Reyrat et al., 1995; Azad et al., 1996), and new protocols allowing easier detection of allelic exchange mutants have also been developed (Norman et al., 1995; Balasubramanian et al., 1996; Pelicic et al., *FEMS Microbiol. Lett.* 1996).

However, as for transposon mutagenesis, detection of very rare allelic exchange events is hindered by low transformation efficiencies and high frequencies of illegitimate recombination. Thus, many genes still remain refractory to allelic exchange by available technology. Clearly, both mutagenesis systems require the design of more efficient methods.

The encountered problems can be circumvented by using a replicative delivery vector, which is efficiently lost under certain conditions. Allowing the introduced delivery vector to replicate avoids the problems arising from low transformation efficiencies. Then, under counter-selective conditions, clones that still contain the vector are eliminated, allowing the detection of very rare genetic events. One such system has been developed: using a conditionally replicative vector, which is efficiently lost at 39° C. in *M. smegmatis*, the first mycobacterial insertional mutant libraries were constructed in this fast-growing model strain (Guilhot et al., 1994). However, the thermosensitive vectors used are only weakly thermosensitive in slow-growing mycobacteria of the *M. tuberculosis* complex and therefore cannot be used in these species for transposon or allelic exchange mutagenesis (unpublished data).

Thus, one embodiment of this invention provides a system, which uses the counter-selective properties of the SacB gene and a Mycobacterial thermosensitive origin of replication, and enables the positive selection of insertion mutants. The basic methodology was first used to deliver derivatives of IS1096 (Cirill et al., into the chromosome of *M. tuberculosis*, leading to the construction of the first transposition mutants libraries for this important pathogen. The libraries were analyzed and seem to be representative.

Once a transposon mutants library of mycobacteria, specifically of pathogenic origin, according to the present invention has been constructed, the recombinant clones that are attenuated in their virulence are selected based on their capacities to multiply in a host in which they have been inoculated.

Because a transposon mutants library contains a number of recombinant clones (in the range of $10^4$ to $10^7$ cfu), selecting clones of interest that have a low multiplication index in the macrophages of the host can require a great deal of work. This is due to the fact that a minimum of five animals have to be infected with a particular clone to ensure its multiplication and immunogenic and/or protective properties. Consequently, it is preferable to use oligonucleotide tags inserted in the transposon that allow the precise identification of every clone. The oligonucleotide tag is a double-stranded polynucleotide of a known sequence, which has a length of 20 to 40 nucleotides. The tags are then ligated into the transposon of interest used to construct the transposon mutants library. This technique allows the administration of more than a hundred recombinant tagged clones simultaneously to the animal (for example Balb/c mice) and the selection of clones that have the desired multiplication properties in the host. The selected clones are then precisely identified by using the oligonucleotide tag sequences as probes. This technique is fully described by Hensel et al. 1995 and Mahan et al., 1993, incorporated herein by reference.

Transposition with the vectors of this invention can also be used for introducing a stable copy of a gene of interest in a mycobacterium strain. The gene of interest is preferably a gene coding for an antigenic protein, thus allowing the cloning of protective antigens, for example in BCG vaccine strains.

Another application for the insertion of transposons (also referred to as insertion sequences) in mycobacterial strains using recombinant vectors according to this invention is random inactivation of genes coding for a protein involved in the virulence of the initial mycobacterial pathogenic strain. Once the gene is identified, compounds of therapeutic value may be screened for properties allowing inactivation of said protein or inactivation of the expression of the identified gene.

Representative embodiments of this invention will be described in more detail in the following examples.

EXPERIMENTAL PROCEDURES FOR ALLELIC EXCHANGE

Bacterial Strains and Media

The bacterial strains and plasmids used in this study are listed in Table 3. *E. coli* was routinely grown on liquid or solid Luria-Bertanl ("L") medium, and kanamycin and gentamicin were used at 20 μg ml$^{-1}$. *M. smegmatis* was grown on liquid Middlebrook 7H9 medium (Difco) supplemented with 0.2% glycerol and 0.05% Tween, or on solid L medium. When required, antibiotics were included at the following concentrations: kanamycin, 20 μg ml$^{-1}$; and gentamicin, 5 μg ml$^{-1}$.

TABLE 3

Bacterial plasmids and strains used in this study.

| Strain/Plasmid | Relevant characteristics | Source/Reference |
| --- | --- | --- |
| Strain | | |
| *E. coli* Dh5α | φ80dlacZΔM15 recA1 endA1 hsdR17 (r$_k^-$,m$_k^-$) | Gibco BRL |
| *M. smegmatis* mc 155 | Highly transformable mutant | Snapper et al. (1990) |
| Plasmid | | |
| pY6001 | pUC19 with the pyrF gene of *M. smegmatis* on a Sau3Al fragment | Husson et al. (1990) |
| pY6002 | Insertion of the aph cassette in BamHl of pY6001 resulting in pyrF::Km | Husson et al. (1990) |
| pJQ200 | Cloning vector with SacB and aacCl | Quandt and Hynes (1993) |
| pPR2b | pjQ200 with pyrF::Km on an Xbal-Mlul fragment of pY6002 | This work |
| pPR33 | Excision of the aph gene from pY6002 and blunting resulting in pyrF$^+$ | This work |
| pPR34 | pJQ200 with pyrF$^+$ on an Xbal-Mlul fragment of pPR33 | This work |

Transformants were selected on LU medium (L medium with 0.2 mM uracil) supplemented with kanamycin (LUK) or gentamicin (LUG). 10% sucrose was added where indicated (LUS or LUKS plates). Uracil auxotrophs were identified by their inability to grow on M63 minimal medium with glucose as the sole carbon source.

DNA Manipulations

Restriction enzymes, T4 DNA polymerase, and T4 DNA ligase were purchased from Boehringer Mannheim, Amersham, and Gibco BRL, respectively. All enzymes were used in accordance with the manufacturer's recommendations. Plasmid DNA was isolated by Qiagen preparation (Qiagen Inc.). DNA fragments used in the cloning procedures and for radiolabelling were gel purified using the Geneclean II kit (BIO 101 Inc.).

Electrotransformation of Bacteria

Electrocompetent bacteria were prepared by the method of Sander et al. (1995) with minor modifications. Bacteria were grown in 400 ml of L (*E. coli*) or 7H9 medium (*M. smegmatis*) to an OD$_{600}$ of). 4. After three washings in 10% glycerol, the cells were resuspended in 1 ml 10% glycerol. Aliquots (100 μl) of freshly prepared mc$^2$155 cells were electroporated with 1 μg of vector DNA in 0.2 cm cuvettes (Bio-Rad) with a single pulse (2.5 kV, 25 μF, 200 ohms). After 3–4 days of incubation, single colonies were picked and resuspended in 7H9 medium aliquoted in 96-well microtitre plates. Forty-eight clones were replicated simultaneously on different selective media using a replica plater (Sigma).

Isolation of Genomic DNA, and Southern Analysis

Mycobacterial genomic DNA was isolated as follows: cells from a 5 ml culture were pelleted by centrifugation (15 min, 5000×g). The pellet was resuspended in 250 μl of solution 1 (25% sucrose, 50 mM Tris-HCl pH 8.0, 50 mM EDTA, 500 μg ml$^{-1}$ lysozyme) and incubated overnight at 37° C. Two hundred and fifty microlitres of solution II (100 mM Tris-HCl pH 8.0, 1% SDS, 400 μg ml$^{-1}$ proteinase K) was then added and the samples incubated for 4h at 55° C. DNA was then extracted twice with phenol-chloroform, and concentrated by ethanol precipitation.

One microgram of genomic DNA was digested overnight with an excess of restriction enzyme (30 U) and separated by electrophoresis using 0.7% agarose gels. Southern blotting was performed in 20×SSPE (150 mM NaCl, 8.8 mM NaH$_2$PO$_4$, 1 mM EDTA, pH 7.4) using Hybond-N+nylon membranes (Amersham) with standard methods (Sambrook et al., 1989). The Megaprime random-primed labelling kit (Amersham) and 5 μmCl of [α-$^{32}$P]-dCTP were used to label probes. Non-incorporated label was removed by filtration through a Nick Column (Pharmacia). Prehybridization and hybridization were performed at 65° C. using RH buffer (Amersham), as recommended by the manufacturer. Serial 15 min washings were performed at 65° C. as follows: two washes with (2×SSPE, 0.1% SDS), one wash with (1×SSPE, 0.1% SDS) and two washes with (0.7×SSPE, 0.1% SDS). Blots were exposed overnight to X-Omat AR X-ray film (Kodak) at −80° C.

Construction of Vectors pPR26 was constructed by inserting the blunt-ended Xbal-Mlul fragment (5.9 kbp), containing the pyrF::Km allele excised from pY6002 (Husson et al., 1990), into the Smal cut pJO200 vector (Quandt and Hynes, 1993). The aph cassette used to inactivate the pyrF gene was excised from pY6002 by BamHl digestion, and a frameshift mutation was introduced in the pyrF gene (pyrF$^+$) by blunting with the T4 DNA polymerese and religation, resulting in pPR33. pPR34 was constructed by cloning a blunt-ended Xbal-Mlul fragment (4.6 kbp), containing the mutated copy pyrF$^+$, into the Smal site in pJO200.

pYGO01 (Husson et al., 1990) was reconstructed during pPR33 construction, by omitting the blunting step before the religation. The 2.5 kbp Sphl fragment of pY6001 corresponding to the pyrF gene was used as a probe in the Southern-blot experiments.

pPR26 and pPR34 were deposited under the provisions of the Budapest Treaty at the National Collection of Cultures of Microorganisms (C.N.C.M.) in Paris on Jun. 19, 1996 and assigned reference Nos. I-1729 and I 1731, respectively.

Over the last decade, the genetic characterization of mycobacteria has greatly benefited from the development of efficient genetic systems, resulting in the identification of several genes that could play a role in virulence (Jacobs, 1992). However, the construction of defined mutants leading to a better understanding of the physiopathology of tuberculosis is still hampered by the great difficulty to perform allelic exchange (Jacobs et al., 1991).

Due to the rarity of double-crossover events and the high levels of illegitimate recombination, the isolation of a gene exchange mutant is always cumbersome, if possible at all. Despite those difficulties, allelic exchange in the fast-growing *M. smegmatis* has been achieved (Husson et al., 1990) using a traditional protocol of mutagenesis (Ruvkin and Ausubel, 1981); a gene inactivated in vitro by the insertion of an antibiotic resistance marker is delivered on a suicide vector into the bacteria. The proportion of allelic exchange mutants was variable and generally low, representing less than 10% of the transformants Husson et atl, 1990). The ratio, double-crossover to single recombination and illegitimate recombination, is even more unfavorable in slow-growing mycobacteria. This partly explains why the first attempts to perform allelic exchange in mycobacteria from the *M. tuberculosis* complex were unsuccessful (Aldovini et al., 1993; Kalpana et al., 1991).

Nevertheless, it has been demonstrated that allelic exchange was possible in *M. bovis* BCG using the ureC gene coding for a subunit of the urease (Reyrat et al., 1995). Reyrat et al. took advantage of the fact that urease activity can be monitored with a simple colorimetric test, which facilitated the otherwise time consuming screening step of transformants (Reyrat et al., 1995). Ure clones represented only 4% of the transformants. Simultaneously, two other groups succeeded in identifying low-frequency allelic exchange in slow-growing mycobacteria (Marklund et al., 1995; Norman et al., 1995).

The overall proportion of double recombinants is thus generally lower than *M. smegmatis* and it depends essentially on the selected gene. Moreover, the frequency of homologous recombination for several different genes leud (Balasubramanian et al., 1996), purC (Jackson, pers. comm.), is too low to enable the detection of double recombinants in a classical gene exchange experiment (Ruvkin and Ausubel, 1981).

Expression of SacB is lethal to mycobacteria in the presence of sucrose SacB, making it a useful counter-selectable marker for positive selection of gene replacement events as demonstrated in the fast-growing *Mycobacterium smegmatis*. Following the same methodology, a sucrose counter-selectable vector was used to deliver, into the Mycobacterium bovis BCG genome, an inactivated copy (ureC::Km) of the ureC gene encoding the mycobacterial urease. A two-step selection procedure on 2% sucrose allowed the positive selection of gene exchange mutants. This technique should thus be an extremely useful facility for the genetic analysis of pathogenic mycobacteria.

Selection of a UreC Single-Recombinant

As for the experiments in *M. smegmatis*, the sucrose counter-selectable suicide vector we used was pJQ200 (Quandt and Hynes, 1993). The ureC::Km mutated allele was excised from pJΔ64% (Reyrat et al., 1995) on a SacI-KpnI fragment, which was made blunt-ended and inserted into SmaI-cut pJQ200 to give rise, following the orientation of the insert, to pPR24 or pPR25. pPR24 was selected at random for the subsequent experiments and used to transform *M. bovis* BCG by electroporation. However, the results are similar when using pPR25 (data not shown).

The transformants, resulting either from homologous or illegitimate recombination of pPR24 into the chromosome, were selected on 7H10 medium supplemented with kanamycin. The electroporation of one µg of closed circular (cc) pPR24 vector resulted in approximately 200 transformants, thus the frequency of transformation was similar to that when pJΔ64% was used (Reyrat et al., 1995). Transformant colonies were phenotypically characterized using the urea/indol calorimetric test (Meyer and David, 1979): a red coloration was scored as Ure$^+$, whereas a yellow coloration is considered as Ure$^-$. Only 4% of the transformants were Ure$^-$ and resulted thus from an allelic exchange event (Table 4).

TABLE 4

Effects of the presence of 2% sucrose on the proportion of ureC allelic exchange mutants.

| Medium$^a$ | Percent of total clones (%)$^b$ | |
| --- | --- | --- |
| | Ure$^{-c}$ | Ure$^{+c}$ |
| without sucrose (one step) | 4 | 96 |
| with 2% sucrose (two-step) | 26 | 74 |

$^a$The selective medium was 7H10 supplemented with kanamycin (20 µg.ml$^{-1}$).
$^b$50 clones were analyzed.
$^c$Ure$^-$: no change of color; Ure$^+$: change of the color to red.

The results were absolutely in accord with what was already described by Reyrat et al. in the initial allelic exchange experiments (Reyrat et al., 1995).

Figure 4:
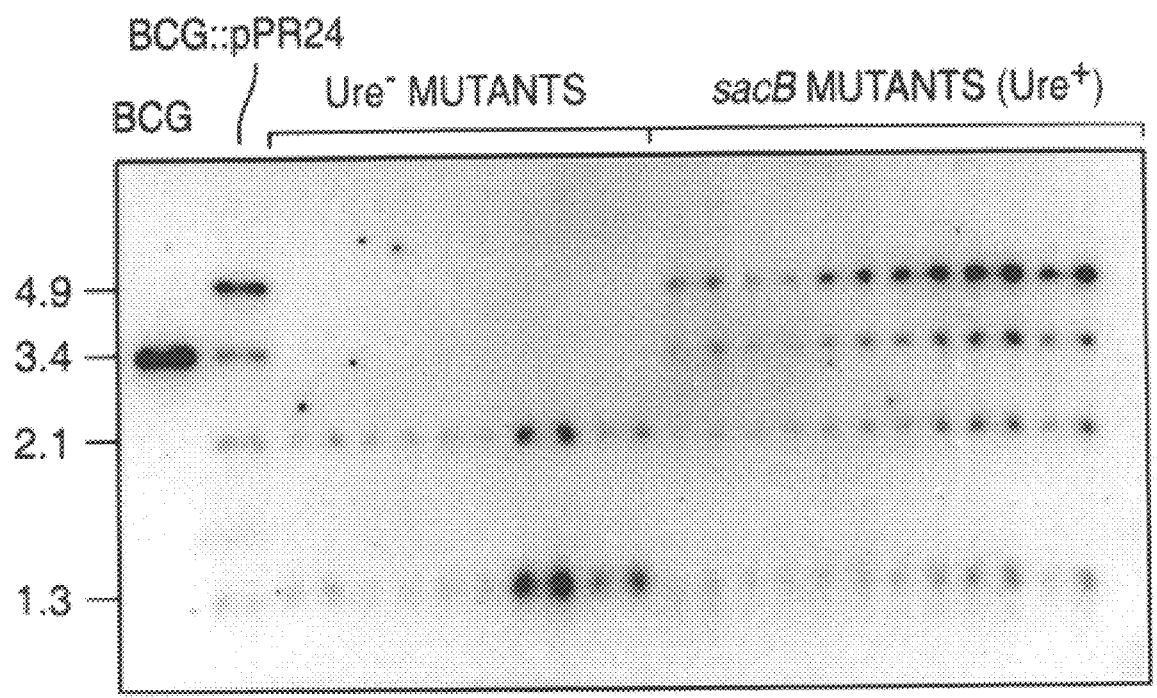

For a two-step selection on sucrose as described above for *M. smegmatis* (Pelicic et al., *Mol. Microbiol.* 1996), one needs to select a clone corresponding to a single-recombination event in the target gene. Five randomly chosen Ure$^+$ transformants were propagated in 7H9 until saturation. The genomic DNA was extracted and analyzed by Southern-blotting using the vector pPR24 as a probe. Surprisingly, all the clones corresponded to single homologous recombination event and contained a complete copy of pPR24 inserted into the ureC gene (FIG. 4). This is in contrast with what was described in previous allelic exchange attempts with other genes, where the vast majority of the analyzed clones, up to 80%, resulted from illegitimate rather than homologous recombination (Aldovini et al., 1993; Kalpana et al., 1991). The differences could possibly be due to the length and the structure of the genes that have been employed.

pPR24 and pPR25 were deposited under the provisions of the Budapest Treaty at the National Collection of Cultures of Microorganisms (C.N.C.M.) in Paris on Jun. 19, 1996 and assigned reference Nos. I-1727 and I-1728, respectively.

Two-Step Positive Selection of Allelic Exchange Mutants

Figure 5:
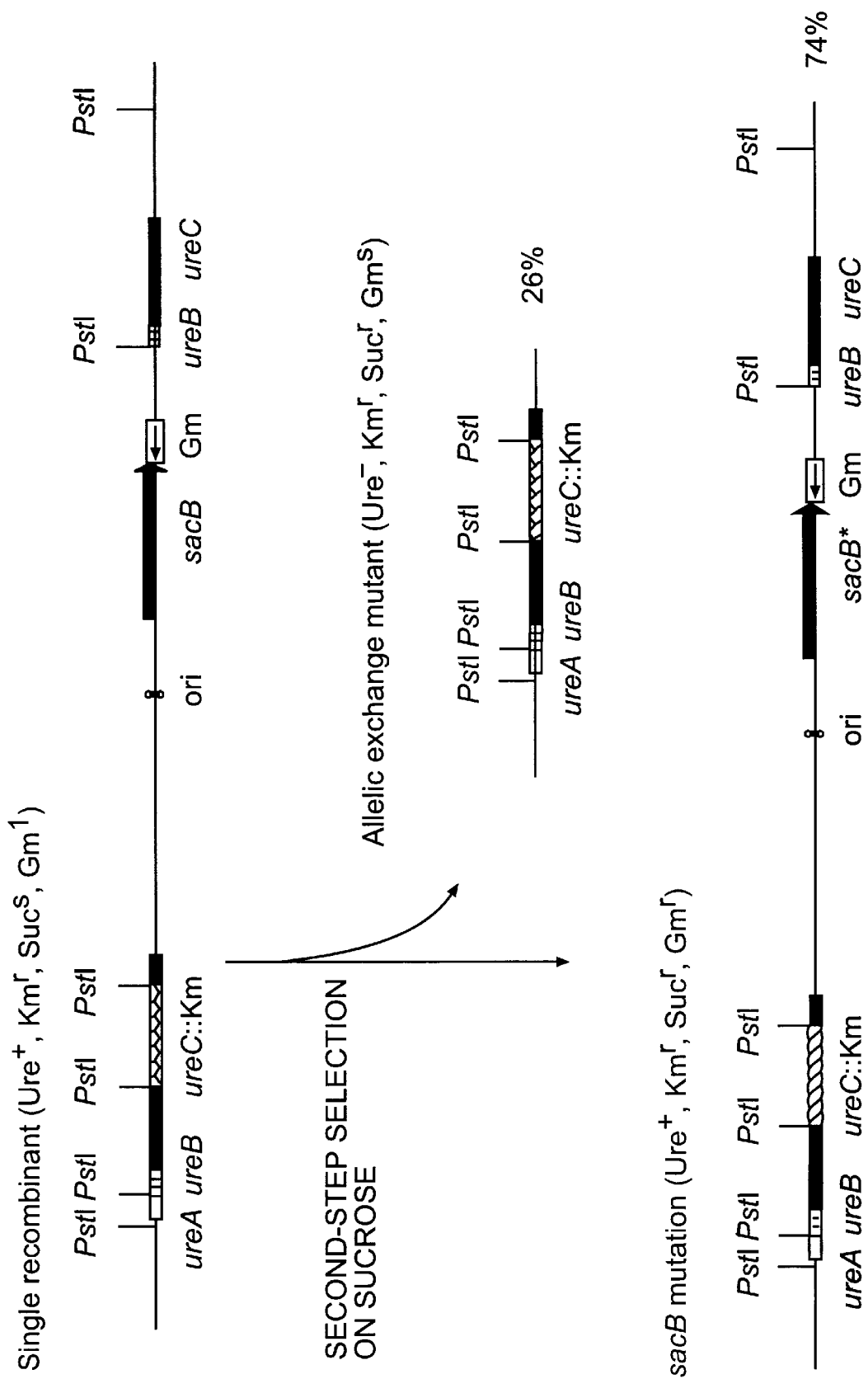
Figure 6:
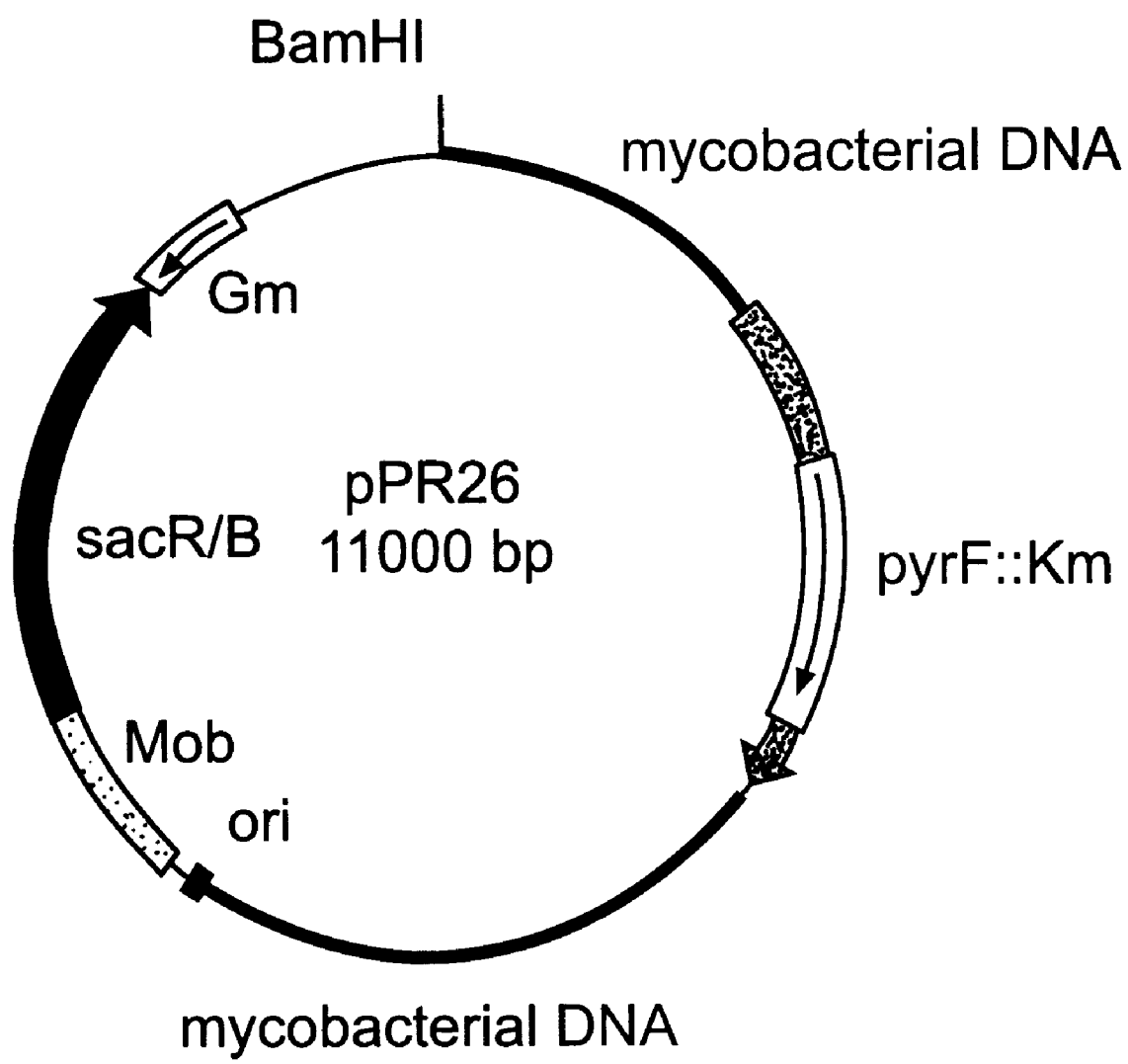
Figure 7:
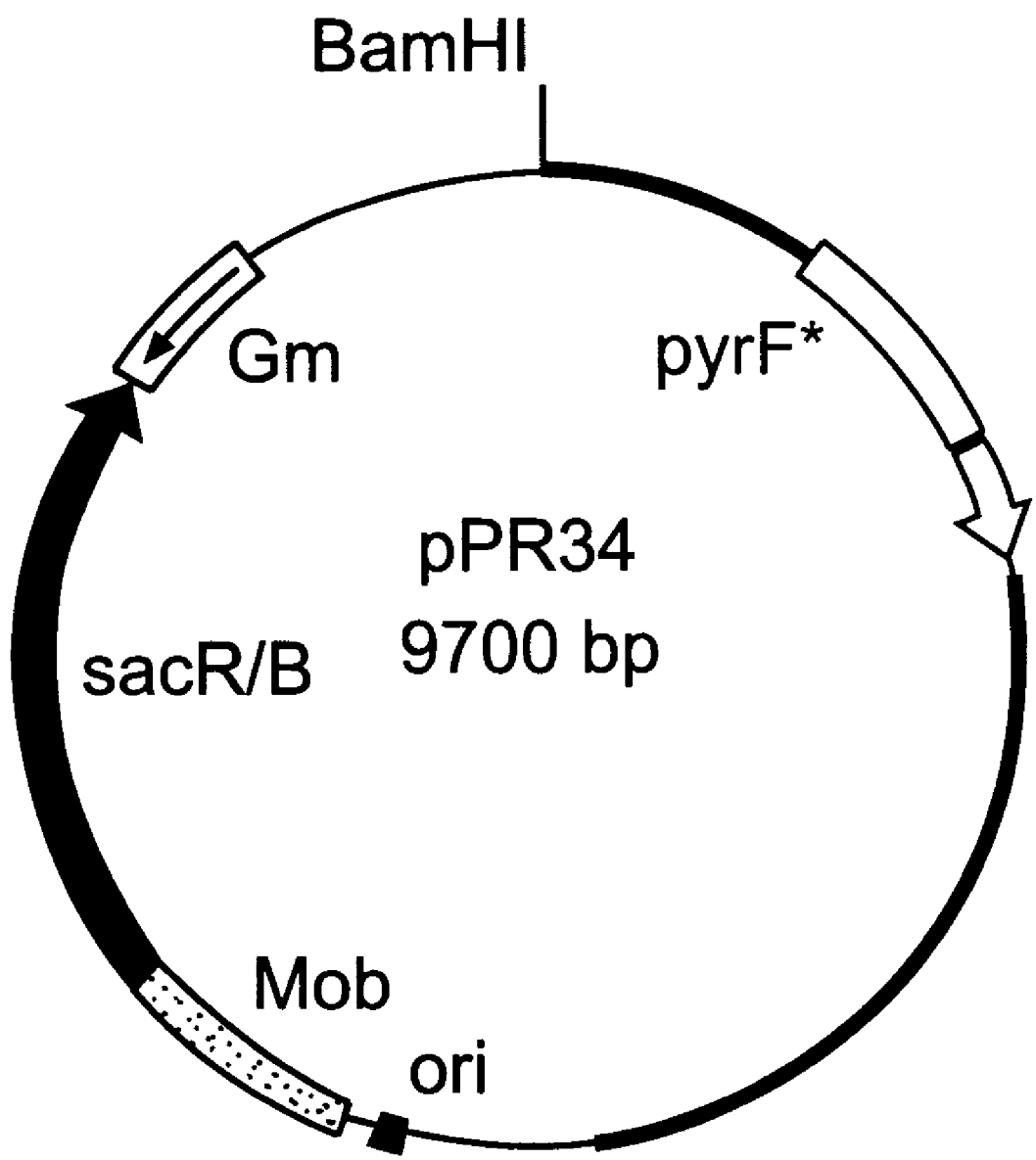
Figure 8:
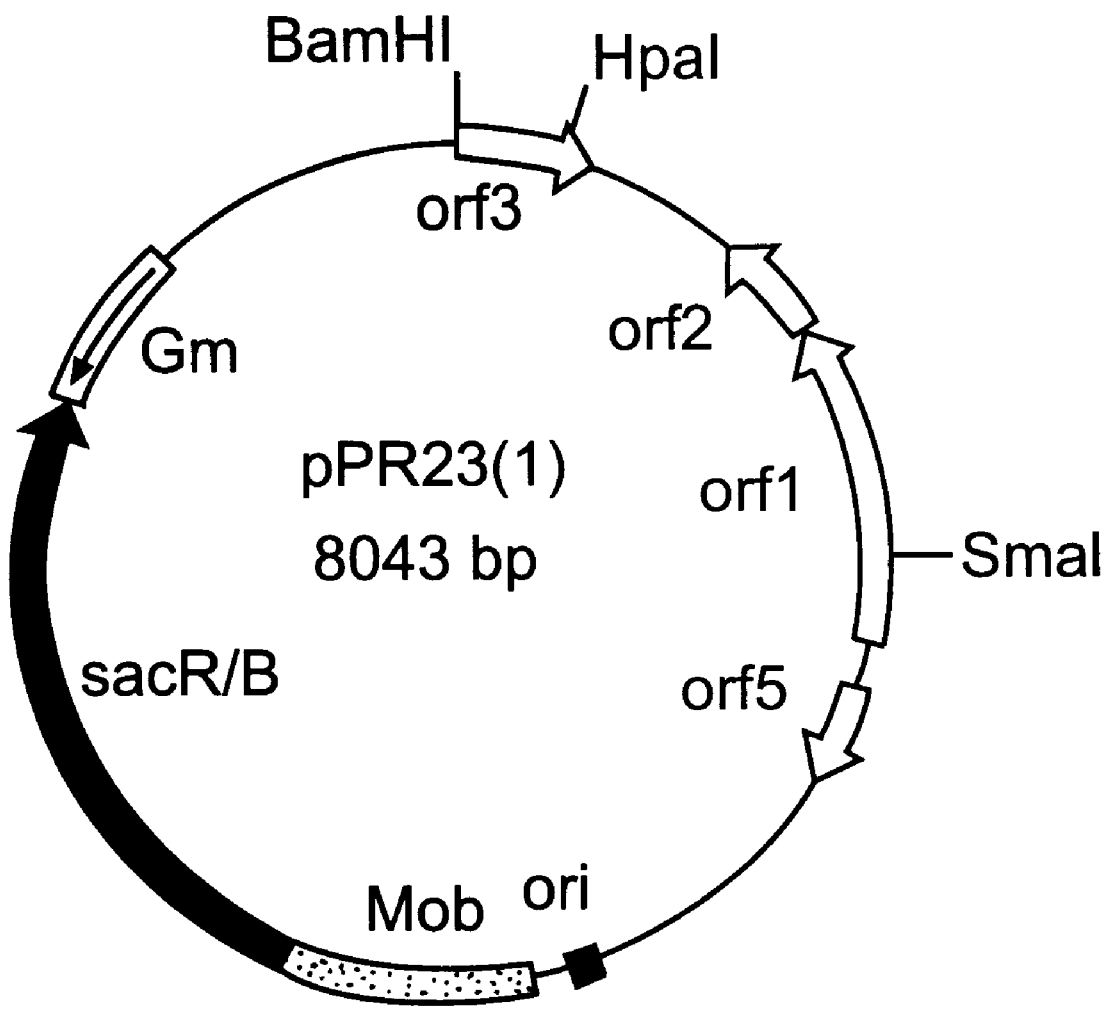
Figure 9:
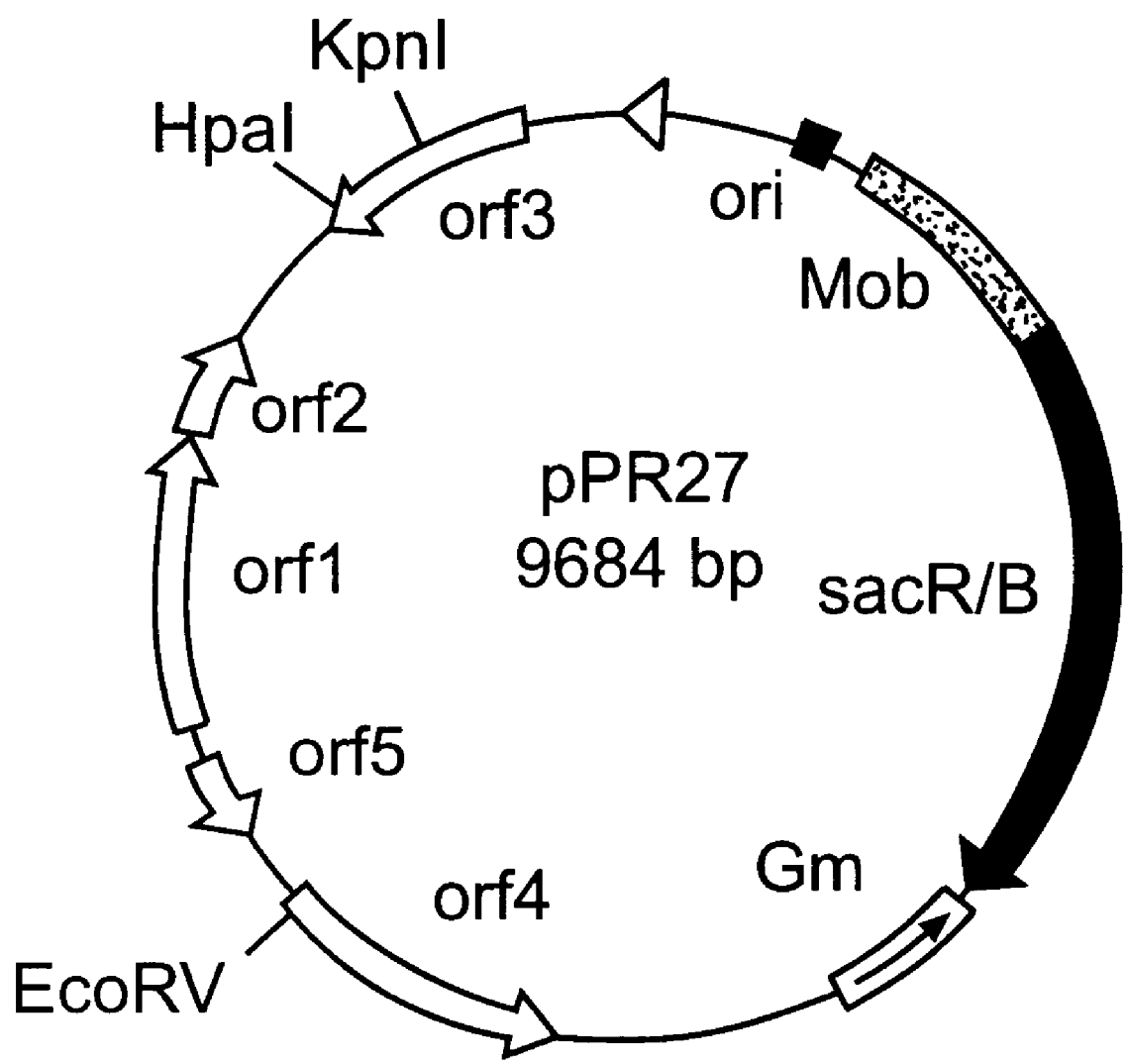
Figure 10:
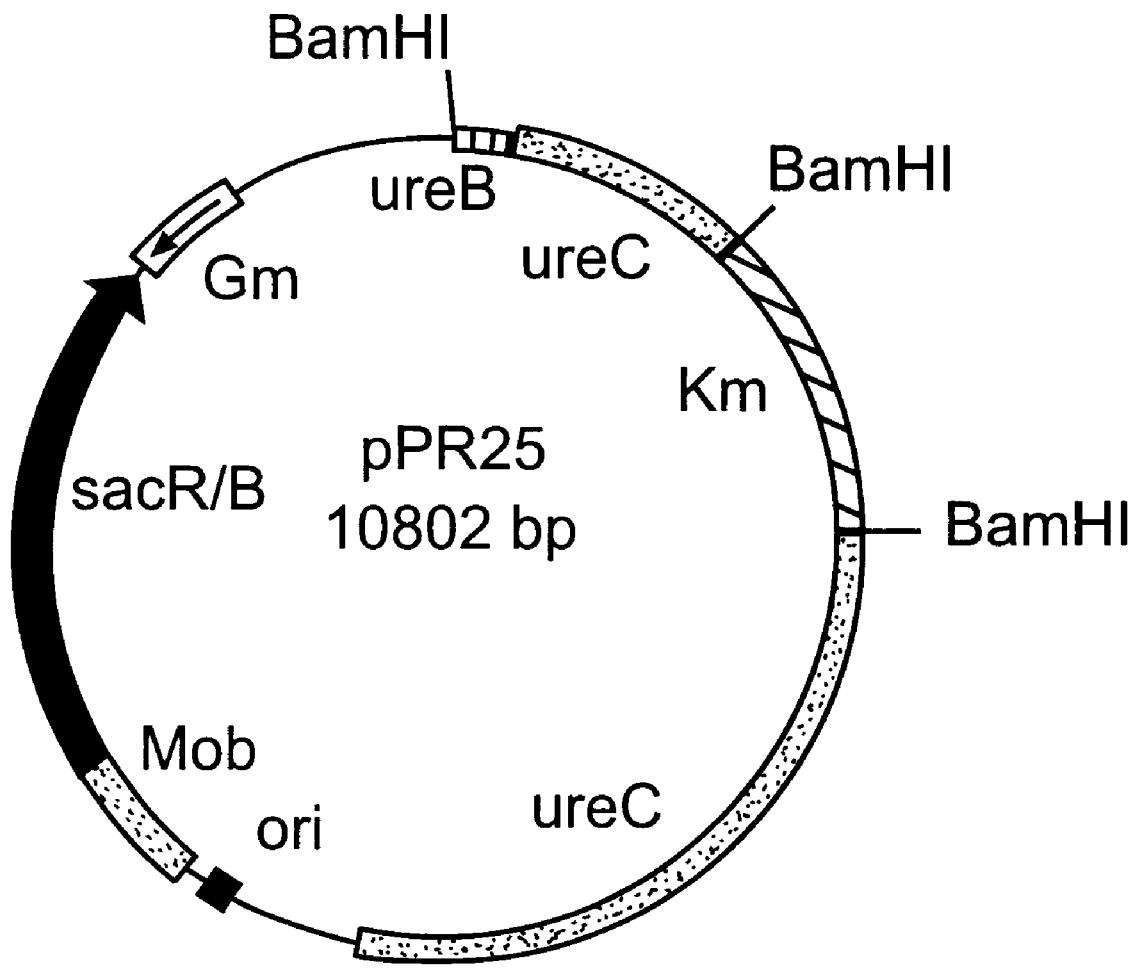
Figure 11:
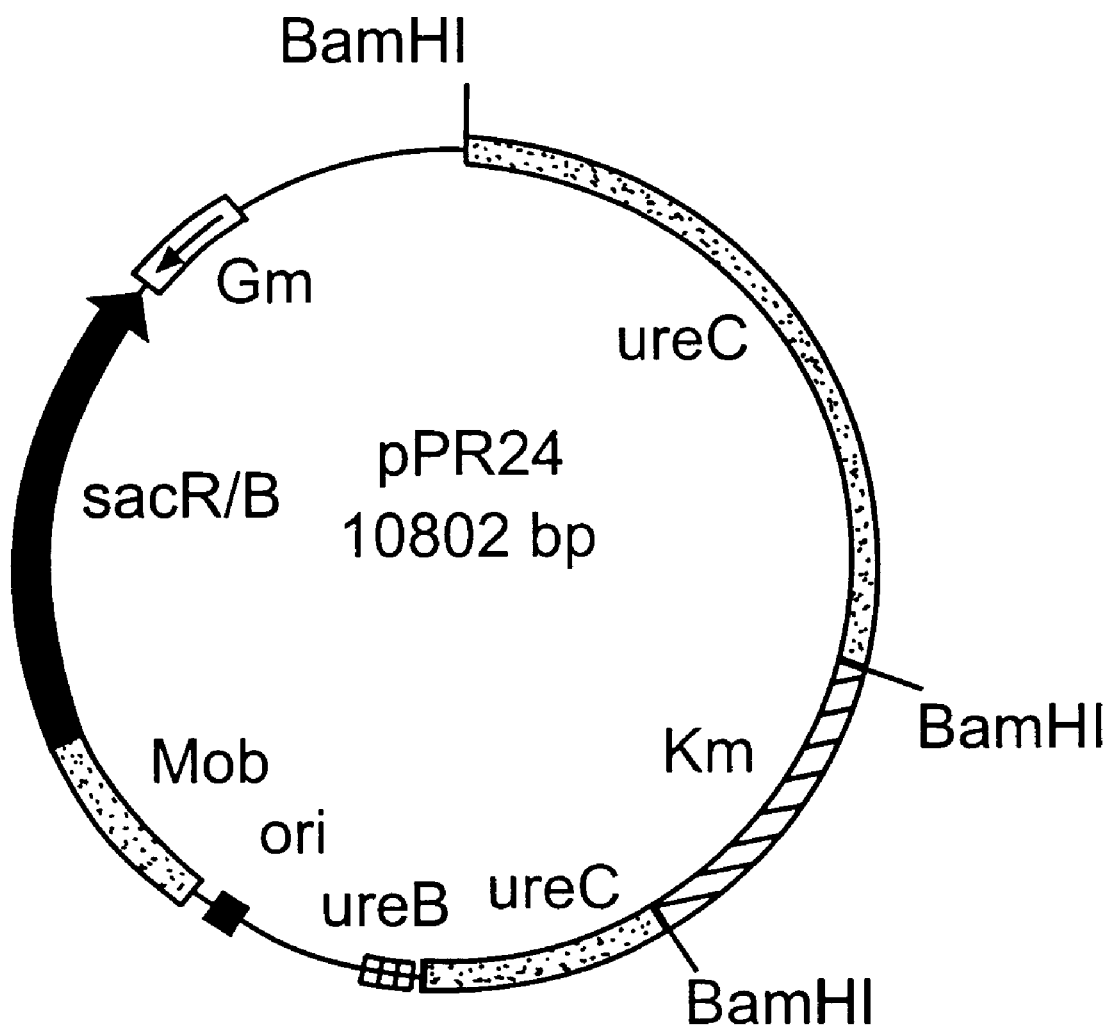
Figure 12:
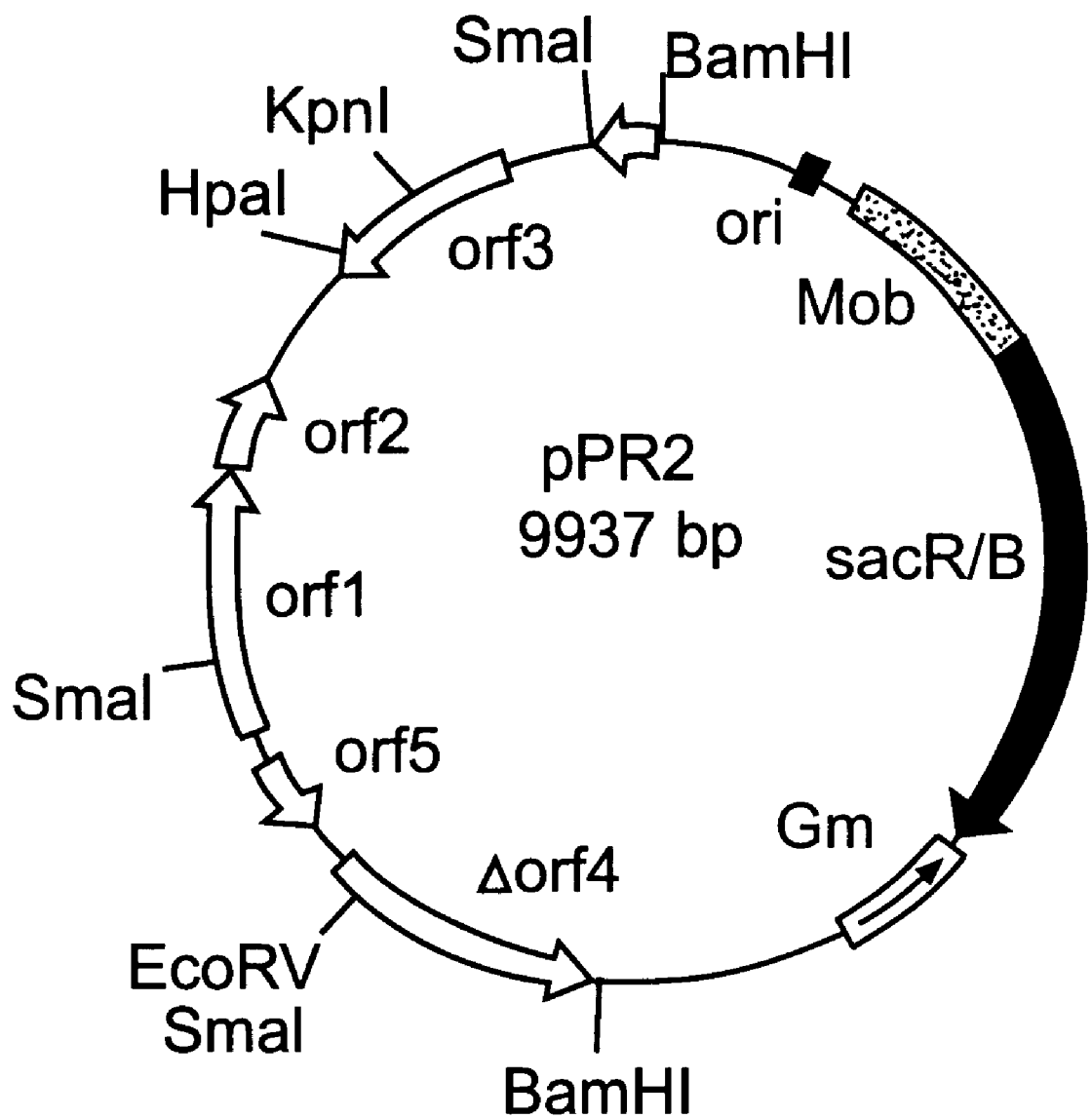

When propagated in 7H9 without antibiotic, the above described single-recombinants could undergo two changes that would render them Km$^r$, Suc$^r$: (i) cells may lose the SacB gene during a second cross-over, (ii) SacB may be inactivated by a point mutation, a deletion or an insertion (FIG. 5). The frequency of the second homologous recombination event is very low, and was estimated at $10^{-5}$ in *M. smegmatis* for the pyrF gene (Husson et al., 1990). Thus the detection of an allelic exchange mutant, though possible for a gene with a defined and an easily screenable phenotype is virtually impossible for the vast majority of genes where the screening is based on a Southern-blot experiment.

Cultures of the single recombinant clones were spread, at a 1/50 dilution, on 7H10-Km supplemented with 2% sucrose. In contrast to our previous experiments (Pelicic et al., *J.*

Bacteriol. 1996; Pelicic et al., Mol. Microbiol. 1996), the concentration of sucrose was lowered to 2% because the growth of untransformed M. bovis BCG is dramatically slowed down in the presence of 10% sucrose (Pelicic et al., J. Bacteriol. 1996). The efficiency of selection remained the same, whereas the growth rate was unaffected on 2% sucrose (Pelicic et al., J. Bacteriol. 1996). 500 Suc$^r$, Km$^r$ colonies were obtained from one ml of culture, and 50 clones were analyzed by the phenotypic test. The proportion of Ure$^-$ mutants was much higher than in a classical experiment presenting a 6-fold increase (Table 4). Approximately one in four colonies tested (26%) corresponded to an allelic exchange mutant as also verified on a Southern-blot (FIG. 4). The remaining clones (74%) though Suc$^r$, were Ure$^-$ and presumably corresponded to clones with a mutation in the SacB gene. Their genomic DNA was probed with pPR24 in a Southern-blot experiment and this showed no apparent change of the vector size, suggesting that the SacB mutations were point mutations or micro-deletions (FIG. 4). Unlike what was observed in M. smegmatis, with the pyrF gene, no mutants corresponding to the insertion of an IS element were observed.

In summary, it has been demonstrated that a two-step positive selection of allelic exchange mutants, using SacB as a counter-selectable marker, is possible and very efficient in the slow-growing M. bovis BCG. As for the results obtained in M. smegmatis using the same protocol, a high proportion of the clones selected on sucrose were allelic exchange mutants. In cases where the allelic exchange is possible using a classical protocol of mutagenesis, one-step selection on sucrose would greatly reduce the number of clones that have to be tested in order to isolate a mutant.

Thus, a general protocol has been designed that should render the creation of defined mutants in bacteria of the M. tuberculosis complex much easier than it was until now, paving the way for further genetic characterization of this important pathogen. Moreover, this protocol should also make possible the creation of unmarked mutants, when the antibiotic resistance cassette in the gene is replaced by a frameshift mutation and the second-step selection is performed on sucrose medium without antibiotic pressure.

EXPERIMENTAL PROCEDURES FOR TRANSPOSON MUTAGENESIS

Bacterial Strains and Culture Conditions E. coli DH5α the strain used in this study for cloning experiments, was routinely grown on liquid or solid Luria-Bertani (L) medium. M. smegmatis mc$^2$155 (Snapper et al., 1990), M. tuberculosis 103 (isolated from a TB patient) and M. bovis BCG Pasteur were grown on liquid Middlebrook 7H9 medium (Difco) supplemented with 0.2% glycerol and 0.05% Tween, or on solid Middlebrook 7H10 medium (Difco). When required, antibiotics were included at the following concentrations: kanamycin (20 Ag. ml$^{-1}$) and gentanticin (5 μg.ml$^{-1}$) for mycobacteria, and gentamicin (20 μg.ml$^{-1}$) for E. coli. Where indicated, 10% or 2% sucrose was added for M. smegmatis or bacteria of the M. tuberculosis complex respectively (Pelicic et al., FEMS Microbiol. Lett. 1996; Pelicic et al., J. Bacteriol. 1996).

Electrotransformation

Electrocompetent cells were prepared as described above but with minor modifications. M. tuberculosis and M. bovis BCG were grown in 200 ml of 7H9 medium to an OD$_{600}$ of 0.4. Cells were washed three times in 10% glycerol and resuspended in 1 ml l10% glycerol. Aliquots (100 μl) of freshly prepared competent cells were electroporated in the presence of 1 μg of vector DNA in 0.2 cm cuvettes (Biorad) with a single pulse (2.5 kV; 25 pF; 200 ohms). Five ml of fresh medium was then added and the culture was incubated at 32° C. for 24 hours before plating, to allow antibiotic resistance expression. Transformants were scored after 7–8 weeks of incubation at 32° C.

DNA Extraction and Southern Analysis

Mycobacterial genomic DNA was isolated as described above but with minor modifications. One hundred μl of D-cycloserine (1 mg.ml$^{-1}$) was added to a 10 ml saturated culture which was then incubated overnight at 37° C. Cells were pelleted by centrifugation (15 min, 5000×g). The pellet was resuspended in 250 μl of solution I (25% sucrose; 50 mM Tris-HCl pH 8.0; 50 mM EDTA; 500 μl.ml$^{-1}$lysozyme) and incubated overnight at 37° C. Two hundred and fifty μl of solution II (100 mM Tris-HCl pH 8.0; 1% SDS; 400 μg.ml$^{-1}$ Proteinase K) was then added and the samples incubated for 4h at 55° C. The lysate was then extracted twice with phenol-chloroform and the DNA was concentrated by ethanol precipitation. Approx. one microgram of genomic DNA was digested overnight with an excess of restriction enzyme (30 U) and the fragments separated by electrophoresis through 0.7% agarose gels. Southern-blotting was carried out in 20×SSPE (150 mM NaCl; 8.8 mM NaH$_2$PO$_4$; 1 mM EDTA pH 7.4) using Hybond-N+ nylon membranes (Amersham). The Megaprime random-primed labeling kit (Amersham) and 5 μCi of (α-$^{32}$p) dCTP were used to label probes. Nonincorporated label was removed by filtration through a Nick Column (Pharmacia). Prehybridization and hybridization were carried out at 65° C. using RH buffer (Amersham) as recommended by the manufacturer. Serial 15 min washes were performed at 65° C. as follows: two washes with (2×SSPE; SDS 0.1%); one wash with (1×SSPE; SDS 0.1%); and two washes with (0.7×SSPE; SDS 0.1%). BioMax MS X-ray film (Kodak) was exposed for 4h to the blots at −80° C.

Construction of Genomic Libraries

Chromosomal DNA from transposon mutants was digested with KpnI or BamHI, which do not cut in the transposon, and purified with QIAquick Nucleotide Removal Kit (QIAGBN). A plasmid library was constructed using KpnI- or BamHI-digested and dephosphorylated "ready to clone" pUC18 vectors (Appligene). Transformants corresponding to integrated transposon and flanking sequences were selected on L-kanamycin.

DNA sequencing

Sequences of double-stranded plasmid DNA were determined using a DNA Analysis System model 373 stretch (Applied Biosystems) and the Taq Dye Deoxy Terminator Cycle Sequencing Kit (Applied Biosystems). Outward primers based on IS1096 sequence (Cirillo et al., 1991) were used α 5'-(SEQ ID NO: 1) CTTCCGCTTCTTCTCCGG-3' and β 5'-(SEQ ID NO: 2) CCATCATCGGAAGACCTC-3'.

Construction of Vectors

The thermosensitive origin of replication of pAL5000, present in ts-SacB delivery vectors, was extracted from pB4D* on a 5 kb BamHI (whole pAL5000) or a 3.7 kb EcoRV+KpnI (minimal origin of replication) fragment (Guilhot et al., 1992). The fragments were blunt-ended and cloned into BamHI-cut pJQ200 harboring the SacB gene (Quandt and Hynes, 1993). Both orientations were obtained for the 3.7 kb "short" insert (pPR23-1 and pPR23-2) and only one orientation for the 5 kb insert (pPR27).

Mutagenesis vectors were constructed by inserting blunt-ended HindIII (4 kbp) fragments, containing the IS1096::Km derivatives, excised from pYUB285 and pYUB297 (McAdam et al., 1995), into blunt-ended BamHI-cut pPR23 or pPR27 vectors. Five different mutagenesis vectors were obtained, pPR28 to pPR32, according to the delivery vector (pPR23 or pPR27), the transposon (Tn5367 or Tn5368) used, and the orientation of the transposon.

Plasmids pPR23 and pPR27 were deposited under the provisions of the Budapest Treaty at the National Collection of Cultures of Microorganisms (C.N.C.M.) in Paris on Jun. 19, 1996 and assigned reference Nos. I-1726 and I-1730, respectively.

IS1096::Km was deposited under the provisions of the Budapest Treaty at the National Collection of Cultures of Microorganisms (C.N.C.M.) in Paris on Jun. 6, 1997 and assigned reference No. I-1874.

Figure 13:
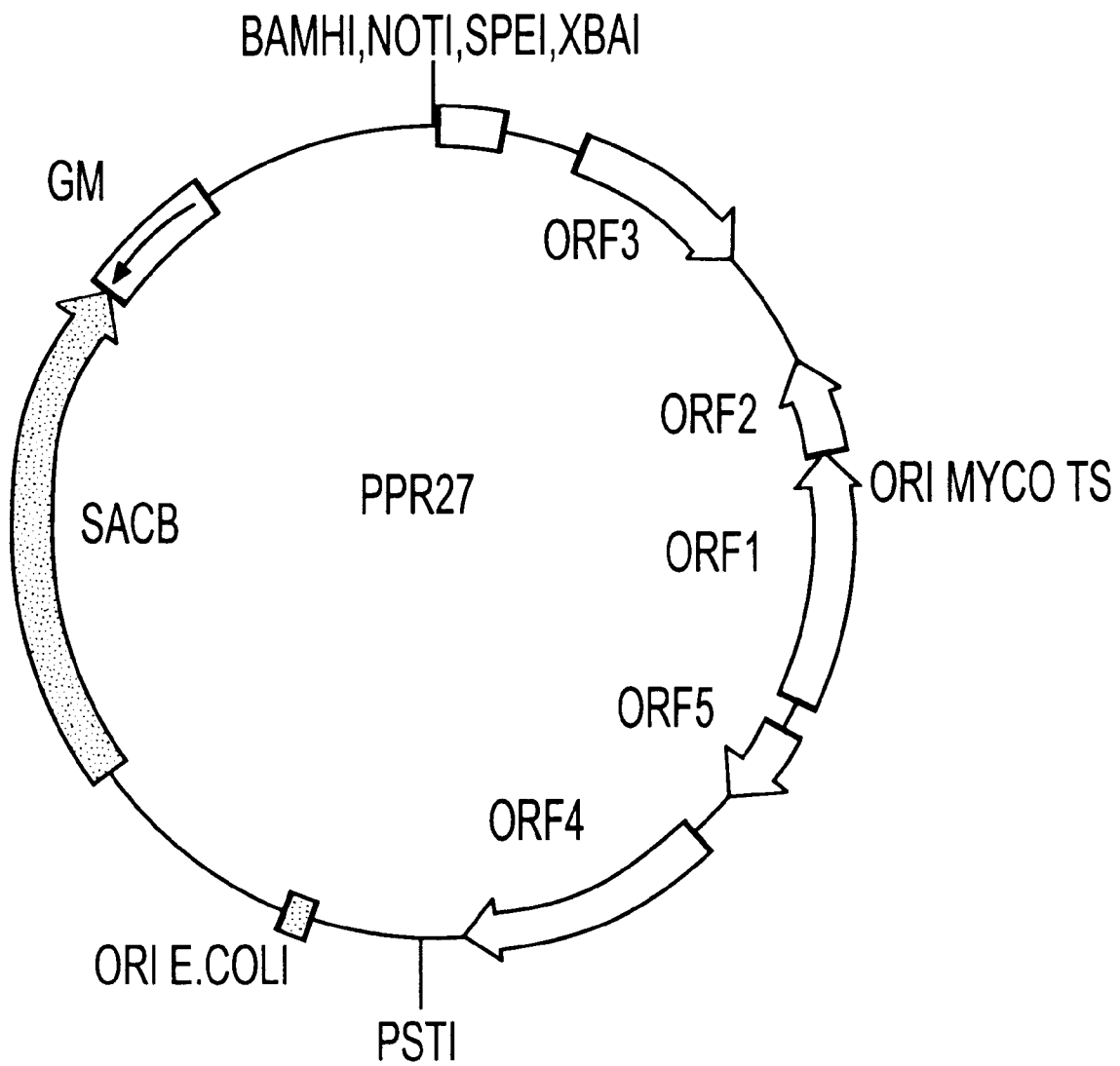

Design and Testing of a Novel Methodology for the Selection of Insertional Mutants As discussed above, we have now demonstrated that expression of the SacB gene from B. subtilis is lethal to mycobacteria in the presence of sucrose. SacB can, therefore, be used as a counter-selectable marker. We therefore tested whether SacB could be used for the positive selection of insertional mutants. A series of conditionally replicative vectors, combining the counter-selective properties of the SacB gene and a mycobacterial thermosensitive origin of replication were constructed (FIG. 13). These ts-SacB vectors were introduced into M. smegmatis mc²155 by electroporation (Snapper at al., 1990). M. smegmatis transformants, selected at 32° C. on 7H10-gentamycin, were grown in 7H9 at 32° C. until saturation. The efficiency of the different counter-selections were then estimated by plating 100 μl samples of these cultures at different temperatures on 7H10-gentamycin plates with or without 10% sucrose, and counting colonyforming units (CFU). Stability of the pAL5OOO thermosensitive origin of replication was measured by plating samples at 39° C., the restrictive temperature for replication, without sucrose addition. The efficiency of SacB counter-selection was estimated by plating samples at 32° C. in the presence of 10% sucrose. By plating on sucrose plates at 39° C., the global counter-selection was assessed (Table 5). Each of the counter-selective pressures, sucrose and growth temperature, was individually low and led to only a limited loss of the vector. However, when transformants were counter-selected for both SacB and the thermosensitive origin of replication, the efficiency of counter-selection was extremely high (Table 5).

TABLE 5

Effect of sucrose and temperature on growth of M. smegmatis transformed with pPR27.[a]

| Growth conditions | CFU per 100 μl | Counterselection efficiency |
|---|---|---|
| 32° C. | $1.2 \times 10^7$ | — |
| 39° C. | 5000 | $4.2 \times 10^{-4}$ |
| sucrose at 32° C. | 3000 | $2.5 \times 10^{-4}$ |
| sucrose at 39° C. | 6 | $5 \times 10^{-7}$ |

[a]Identical results were obtained for pPR23 (data not shown).

This result suggested that ts-SacB vectors could be used to deliver a transposon or a mutated allele into the chromosome of M. tuberculosis allowing the construction of insertional mutant libraries or gene exchange mutants respectively. This protocol of selection was used for all subsequent mutagenesis experiments. Because transformants are grown under permissive conditions, problems due to low transformation efficiencies are avoided. During this step of replication, mutants arising by allelic exchange or transposition can accumulate, overcoming problems due to low frequencies of allelic exchange and transposition. Finally, the great majority of the clones that still contain the vector are eliminated, strongly increasing the proportion of mutants among the survivors.

Figure 14:
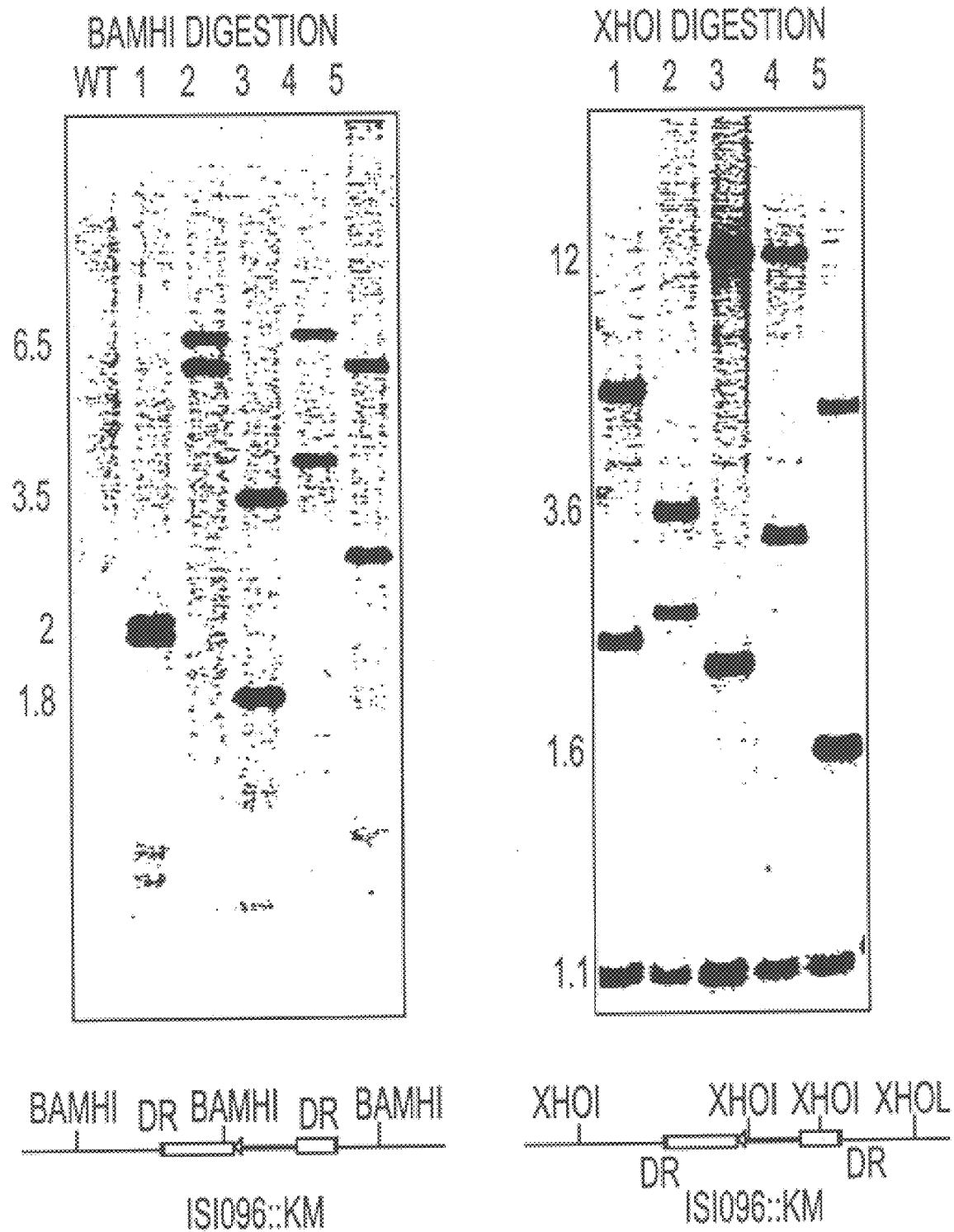

Construction of Transposition Mutants Libraries of M. tuberculosis and M. bovis BCG ts-SacB vectors were first tested for transposon mutagenesis in bacteria of the M. tuberculosis complex. The devised selection protocol implies that the delivery vector, containing the counter-selectable SacB gene, should be lost upon transposition such that transposition mutants can be positively selected. In other words, the transposon to be used should transpose in a conservative fashion (McAdam et al., 1994). The only known mycobacterial mobile element suitable for our system was IS1096 (Cirillo et al., 1991): it is not found in the chromosomes of the M. tuberculosis complex mycobacteria; and its transposition is random and mostly conservative. Moreover, derivatives of IS1096, with a kanamycin resistance cassette inserted into the mobile element (IS1096::Km), are able to transpose in M. bovis BCG (McAdam et al., 1995). Two different IS1096 derivatives, Tn5367 and Tn5368, were cloned into pPR23 and pPR27 delivery vectors giving a series of mutagenesis vectors which were introduced in M. tuberculosis 103 and M. bovis BCG Pasteur by electroporation. The selection strategy described above was used. Putative insertional mutants, in which IS1096::Km may have transposed onto the chromosome, were selected at 39° C. on 7H10-kanamycin+ 2% sucrose plates. When an initial inoculum of $10^7$ bacteria was plated, $10^4$ and $10^5$ colonies were obtained for M. tuberculosis and the vaccinal strain respectively. Five randomly picked M. tuberculosis (pPR32) transformants were analyzed by Southern-blot, using pPR32 as a probe. Two hybridizing fragments of varying sizes were expected when BamHI was used (FIG. 14). As XhoI cuts twice in IS1096::Km, transposition mutants were expected to present three hybridizing fragments (FIG. 14): one fragment of conserved length, internal to the mobile element, and two fragments the sizes of which would differ between the mutants provided that the transposition was random. The hybridization patterns for all the clones tested were in agreement with the transposition of Tn5368 onto the chromosome of the tubercle bacillus (FIG. 14). This was also confirmed with other restriction enzymes (data not shown). The same blot was analyzed with the delivery vector as a probe, ie. pPR27 which contains no inserted transposon. No hybridization signal was detected (data not shown), confirming that the delivery vector had been lost during transposition. Independent transposition experiments were repeated at least five times in both M. tuberculosis and M. bovis BCG and similar Southern hybridization results were obtained for all the mutagenesis vectors. More than two hundred mutants were examined by Southern-blot analysis, and greater than 95% of the clones resulted from the transposition of IS1096::Km onto the chromosome. However, it should be noted that in some experiments, several clones exhibited the same hybridization patterns, suggesting that they were siblings. This was not unexpected, as the mutagenesis protocol contains a step during which possible mutants are able to replicate. Nevertheless, most of the hybridization patterns of different clones were unique, suggesting that IS1096 transposition occurred at random as previously described (McAdam et al., 1995).

To confirm the randomness of the transposition, several insertion sites were cloned and sequenced. Direct repeats (DR) bracketing the transposon were found, confirming that the clones indeed resulted from transposition events (FIG. 15). Two clones, myc3 and myc6, presented imperfect DRs probably resulting from replication errors. Moreover, DRs were of different lengths between M. tuberculosis and M. bovis BCG mutants: 7bp and 8bp respectively. This is, to our knowledge, the first report of such a phenomenon: DR-length being specific for the strain in which transposition occurs. The mechanism responsible for this strain-specificity is so far unknown. Importantly, despite a preference for A+T rich targets, IS1096 does not appear to display site-specificity as all the analyzed insertion sites were different (FIG. 15).

These results confirmed that the ts-SacB vectors are indeed suitable for delivering transposons onto the chromosome of bacteria of the M. tuberculosis complex. Moreover, the methodology is reliable and fully reproducible, enabling the construction of insertional mutant libraries containing greater than $10^6$ different transposition mutants.

In summary, the present invention provides, for the first time, a single, very simple system which can be used for easy mutagenesis of *M. tuberculosis* either by allelic exchange or by transposition. ts-SacB vectors were successfully used to deliver a mycobacterial transposon into the chromosome of two bacteria of the *M. tuberculosis* complex: *M. tuberculosis* and *M. bovis* BCG. The great majority of the selected clones (more than 95% ) were insertional mutants, with a copy of IS1096::Km inserted in their chromosome. Moreover, Southern-blot analysis (FIG. 14) and sequencing of the flanking regions (FIG. 15) indicate that the mutant libraries, numbering greater than $10^6$ mutants and containing transposons inserted in various sites, are representative. It seems likely that the pool of mutants contains clones in which each of the non-essential mycobacterial genes, numbering 3,000, have been mutated at least once. These libraries will therefore be extremely useful for the identification of avirulent mutants, possibly unable to invade epithelial cells or to replicate in macrophages, in which essential virulence factors have been disrupted (work in progress).

The present invention should greatly contribute to the genetic analysis of *M. tuberculosis* pathogenicity following Koch's molecular postulates (Falkow, 1988; Jacobs, 1992): it allows creation of deemed mycobacterial mutants either by allelic exchange or transposon mutagenesis both of which were previously difficult, or even unfeasible. It opens the way not only to studying the roles in pathogenicity of defined mycobacterial genes, which may or not present similarities to known virulence factors from other bacterial pathogens, but also to the rational construction of attenuated strains, which could be more effective than the BCG as antituberculous vaccines.

REFERENCES

Aldovini, A., Husson, R. N., and Young, R. A. (1993) The uraA locus and homologous recombination in *Mycobacterium bovis* BCG. *J. Bacteriol* 175:7282–7289.

Azad, A. K., Sirakova, T. D., Rogers, L. M. & Kolattukudy, P. B. (1996) *Proc. Nat. Acad. Sci. USA* 93:4787–4792.

Balasubramanian, V., Pavelka, Jr. M. S., Bardarov, S. S., Martin, J. Weisbrod, T. R., McAdam, R., Bloom. B. R., and Jacobs, Jr. W. R. (1996) Allelic exchange in *Mycobacterium tuberculosis* with long linear recombination substrates. *J. Bacteriol* 178:273–279.

Cai, Y., and Wolk, P. C. (1990) Use of a conditionally lethal gene in Anabaena sp. strain PCC7120 to select for double recombinants and to entrap insertion sequences. *J. Bacteriol* 172:3138–3145.

Clanciotto, N. P., Long, R., Eisenstein, B. I., and Engleberg, N. C. (1988) Site-specific mutagenesis in Legionella pneumophila by allelic exchange using counter-selectable ColE1 vectors. *FEMS Microbiol Lett* 56:203–208.

Cirillo, J. D. Barletta, R. G., Bloom, B. R., and Jacobs, Jr, W. R. (1991) A novel transposon trap for mycobacteria: isolation and characterization of IS1096. *J. Bacteriol* 173:7772–7780.

Desomer, J., Crespi. M., and Van Montagu. M. (1991) Illegitimate integration of non-replicative vectors in the genome of Rhodococcus fascians upon electrotransformation as an insertional mutagenesis system. *Mo Microbiol* 5:2115–2124.

Donnenberg, M. S., and Kaper, J. B. (1991) Construction of an ese deletion mutant of enleropathogenic *Escherichia coli* by using a positive-selection suicide vector. *Infect Immun* 59:4310–4317.

Falkow, S. (1988) Molecular Koch's postulates applied to microbial pathogenicity. *Rev Infec Dis* 10:S274-S276.

Gay, P., Le Coq, D., Steinmetz, M. Berkelman, To., and Kado C. I. (1985) Positive selection procedure for entrapment of insertion sequence elements in Gram-negative bacteria. *J. Bacteriol* 164:918–921.

W,. Guilhot, C., Otal, I., van Rompaey, I., Martin, C. & Gicquel, B. (1994) *J. Bacteriol.* 176:535–539.

Guilhot, C., Gicquel, B. & Martin, C., (1992) *FEMS Microbiol. Lett*. 98:181–186.

Hensel, M., Shea, J. E., Gleeson, C., Jones, M. D., Dalton, E. & Holden, D. W. (1995) Simultanious identification of bacterial virulence genes by negative selection. Science. 269:__.

Husson, R. N., James, B. E., and Young, R. A. (1990) Gene and expression of foreign DNA in mycobacteria. *J. Bacteriol.* 172:519–524. *Jacobs, Jr., W. R. (*1992) Advances in mycobacterial genetics: new promises for old diseases. *Immunobiology* 184:147–156.

Jacobs, Jr., W. R., Kalpana, G. V., Cirillo, J. D., Pascopella, L., Snapper, S. B., Udani, R. A., Jones, W. Barletta, R. G., and Bloom, B. R. (1991) Genetic systems for mycobacteria, *Meth Enzymol* 204:537–555.

Jackson, M., Personal communication.

Kalpana, G. V., Bloom, B. R., and Jacobs, Jr. W. R. (1991), Insertional mutagenesis and illegitimate recombination in mycobacteria. *Proc Natl Acad Sci USA* 88:5433–5437.

Kamoun, S., Tola, E., Kamdar, H., and Kado, C.I. (1992). Rapid generation of directed and unmarked deletions in Xanthomonas. Mol Microbiol 6:809–816.

Kaniga, K., Delor, I., and Cornells, G. R. (1991) A wide-host-range suicide vector for improving reverse genetics in Gram-negative bacteria: Inactivation of the blaA gene of *Yersinla enterocolitca. Gene* 109:137–141.

Mahan, M. J., Slauch, J. M. & Mekalanos, J. J. (1993) Selection of bacterial virulence genes that are specifically induced in host tissues. *Science* 259:685–688.

Marklund, B. I., Speert, D. P., and Stokes, R. W. (1995) Gene replacement through homologous recombination in *Mycobacterium intracellulare. J. Bacteriol* 177:6100–6105.

McAdam, R., Guilhot, C. & Gicquel, B. (1994) in Tuberculosis, ed. Bloom, B. R. (ASM Press, Washington, DC), pp. 199–216.

McAdam, R., Weisbrod, T. R., Martin, J., Scuderi, J. D., Brown, A. M., Cirillo, J. D.,Bloom, B. R., & Jacobs Jr., W. R. (1995) Infect. *Immunol.* 63:1004–1012.

Meyer, L., and David, H. L., (1979) Evaluation de l'activité uréase et de l'activité β-glucosidase pour l'identification pratique des mycobactéries. *Ann. Inst. Pasteur Microbiol.* 130B:323–332.

Norman, E., Dellagostin, O. A., McFadden, J., and Dale, J. W. (1995) Gene replacement by homologous recombination in Mycobacterium bovis BCG. Mol Microbiol 16:755–760.

Pelicic, V., Reyrat, J. M., and Gicquet, P. (1996) Expression of the *Bacillus subtillis* SacB gene confers sucrose sensitivity on mycobacteria. *J. Bacteriol.* 178:1197–1199.

Pelicic, V. J.-M Reyra, and B. Gicquel. (Jun. 11, 1996) Generation of unmarked directed mutations in mycobacteria, using sucrose counter-selectable suicide vectors. *Mol. Microbiol.* 20 (5):919–925.

Pelicic, V., Reyrat, J.-M. & Gicquel, B. (1996) *FEMS Microbiol. Lett.* 144:161–166.

Quandt, J., and Hynes, M. F. (1993) Versatile suicide vectors which allow direct selection for gene replacement in Gramm-negative bacteria. *Gene* 127:15–21.

Reyrat, J. M., Berthet, F.-X, and Gloquel, B. (1995) The urease locus of *Mycobacterium tuberculosis* and its utilization for the demonstration of allelic exchange in *Mycobacterium bovis* bacillus Camette-Guerlin. *Proc Natl Acad Sci USA* 92:8768–8772.

Ried, J. L., and Collmer, A. (1987) An nptl-SacB-sacR cartridge for constructing directed, unmarked mutations in Gram-negative bacteria by marker exchange-eviction mutagenesis. *Gene* 57:239–246.

Ruvkin, G. B., and Ausubel, F. M. (1981) A general method for site-directed mutagenesis in prokaryotes. *Nature* 289:85–88.

Sambrook, J., Fritsch, E. F., and Maniatis, T. (1989) Molecular Cloning: A Laboratory Manual. 2nd edn. Cold Spring Harbor, N.Y.: Cold Spring Harbor Laboratory Press.

Sander, P., Meier, A., and Bottger, E. C. (1995) rpst$^+$ a dominant selectable marker for gene replacement in mycobacteria. *Mol Microbiol* 16:991–1000. Schafer, A., Tauch, a. Jager, W., Kalinowski, J., Thierbach, G., and Pohler, A. (1994) Small mobilizable multi-purpose cloning vectors derived from the *Eschericha coli* pK18 and pK19: selection of defined deletions in the chromosome of *Corynebacterium glutamicum*. *Gene* 45:69–73.

Schweizer, H. P. (1992) Allelic exchange in Pseudomonas aeruginosa using novel ColE1-type vectors and a family of cassettes containing a portable oriT and the counter-selectable *Baillus subtilis* SacB marker. *Mol Microbiol* 6:1195–1204.

Snapper, S. B., Melton, R. E. Mustapha, S. Keiser, To., and Jacobs, Jr., W. R. (1990) Isolation and characterization of efficient plasmid transformation mutants of *Mycobacterium smegmatis*. *Mol Microbiol* 4:1911–1919.

Sorenson et al., (1995) Purification and characterization of a low-molecular-mass T-cell antigen secreted by *Mycobacterium tuberculosis*. *Infect. Immun.* 63 (5):1710–1717.

Soupene, E. Foussard, M. Bolstard, P., Truchet, G., and Batut, J. (1955) Oxygen as a key developmental regulator of Rhizobium melilot $N_2$-fixation gene expression within the alfalfa root nodule. *Proc Nati Acad Sci USA* 92:3759–3763.

Stibitz, S. (1994) Use of conditionally counter-selectable suicide vectors for allelic exchange. *Meth Enzymol* 235:458–465.

WHO (1991) Streptomycin. In drugs used in mycobacterial infections. Geneva: World Health Organization.

---

What is claimed is:

1. A process for inserting a transposon IS1096:Km (C.N.C.M. No. I-1874) in the genome of a slow growing Mycobacterium strain comprising the steps of:

a) providing a vector containing SacB gene coding for levansucrase enzyme and said transposon IS1096:Km:

b) transfecting the slow growing mycobacterium with the vector of step a), thereby producing transformed mycobacteria;

c) selecting clones of the resulting transformed mycobacteria in which said transposon IS1096:Km has been inserted by propagating said clones in a culture medium supplemented with sucrose; and d) isolating a strain in which said transposon IS1096:Km has been inserted.

2. The process as claimed in claim 1, wherein the mycobacterium is *M. tuberculosis*.

3. The process as claimed in claim 1, wherein the mycobacterium is *M. bovis*.

4. The process as claimed in claim 1, wherein the mycobacterium is *M. smegmatis*.

5. A transposon mutants library of mycobacteria that has been constructed with a recombinant vector containing SacB gene coding for levansucrase enzyme and a nucleic acid fragment of interest.

6. The transposon mutants library as claimed in claim 5, wherein the nucleic acid fragment of interest is an insertion sequence.

7. The transposon mutants library as claimed in claim 5, wherein the mycobacterium is *M. tuberculosis*.

8. The transposon mutants library as claimed in claim 5, wherein the mycobacterium is *M. bovis*.

9. The transposon mutants library as claimed in claim 5, wherein the mycobacterium is *M. smegmatis*.

10. The transposon mutants library as claimed in claim 6, wherein the insertion sequence is a transposon.

11. The transposon mutants library as claimed in claim 10, wherein the transposon is Tn611.

12. The transposon mutants library as claimed in claim 10, wherein the transposon is IS1096:Km (C.N.C.M. No. I-1874).

* * * * *

UNITED STATES PATENT AND TRADEMARK OFFICE
CERTIFICATE OF CORRECTION

PATENT NO.: 6,096,549

DATED: August 1, 2000

INVENTOR(S): Vladimir PELICIC, Jean-Marc REYRAT, Brigitte GICQUEL, Christophe GUILHOT, and Mary JACKSON It is certified that an error appears in the above-identified patent and that said Letters Patent is hereby corrected as shown below:

Title Page, in the Attorney, Agent, or Firm, line 2:
"Gattett" should read --Garrett--.

In Claim 1, col. 23, line 65:
"Mycobacterium" should read --mycobacterium--,

In Claim 1, col. 23, line 67:
"IS1096:KM:" should read --IS1096:KM;--.

Signed and Sealed this

Seventeenth Day of April, 2001

*Attest:*

NICHOLAS P. GODICI

*Attesting Officer*    *Acting Director of the United States Patent and Trademark Office*

SEQUENCE LISTING

```
<160> NUMBER OF SEQ ID NOS: 11

<210> SEQ ID NO 1
<211> LENGTH: 18
<212> TYPE: DNA
<213> ORGANISM: Mycobacterium sp.

<400> SEQUENCE: 1
cttccgcttc ttctccgg                                              18

<210> SEQ ID NO 2
<211> LENGTH: 18
<212> TYPE: DNA
<213> ORGANISM: Mycobacterium sp.

<400> SEQUENCE: 2
ccatcatcgg aagacctc                                              18

<210> SEQ ID NO 3
<211> LENGTH: 26
<212> TYPE: DNA
<213> ORGANISM: Mycobacterium sp.

<400> SEQUENCE: 3
ggctcttcgc agttgagggt gtagag                                     26

<210> SEQ ID NO 4
<211> LENGTH: 26
<212> TYPE: DNA
<213> ORGANISM: Mycobacterium sp.

<400> SEQUENCE: 4
ctctacaccg tcaagtgcga agagcc                                     26
```

-continued

```
<210> SEQ ID NO 5
<211> LENGTH: 14
<212> TYPE: DNA
<213> ORGANISM: Mycobacterium sp.

<400> SEQUENCE: 5
ccattaccca ttac                                                        14

<210> SEQ ID NO 6
<211> LENGTH: 14
<212> TYPE: DNA
<213> ORGANISM: Mycobacterium sp.

<400> SEQUENCE: 6
aaaaaacaaa aaac                                                        14

<210> SEQ ID NO 7
<211> LENGTH: 14
<212> TYPE: DNA
<213> ORGANISM: Mycobacterium sp.

<400> SEQUENCE: 7
tgattaccga ttac                                                        14

<210> SEQ ID NO 8
<211> LENGTH: 14
<212> TYPE: DNA
<213> ORGANISM: Mycobacterium sp.

<400> SEQUENCE: 8
cattagccat tagc                                                        14

<210> SEQ ID NO 9
<211> LENGTH: 16
<212> TYPE: DNA
<213> ORGANISM: Mycobacterium sp.

<400> SEQUENCE: 9
gaattagcga attagc                                                      16

<210> SEQ ID NO 10
<211> LENGTH: 16
<212> TYPE: DNA
<213> ORGANISM: Mycobacterium sp.

<400> SEQUENCE: 10
gtcaaacggt caaacc                                                      16

<210> SEQ ID NO 11
<211> LENGTH: 16
<212> TYPE: DNA
<213> ORGANISM: Mycobacterium sp.

<400> SEQUENCE: 11
ccattaggcc attagg                                                      16
```